(12) United States Patent
Patel et al.

(10) Patent No.: US 11,602,564 B2
(45) Date of Patent: *Mar. 14, 2023

(54) METHOD FOR STABILIZATION AND DELIVERY OF THERAPEUTIC MOLECULES

(71) Applicants: Nayan Patel, La Habra, CA (US); Chinh Tran, La Habra, CA (US)

(72) Inventors: Nayan Patel, La Habra, CA (US); Chinh Tran, La Habra, CA (US)

(73) Assignee: Nayan Patel, La Habra, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/737,424

(22) Filed: May 5, 2022

(65) Prior Publication Data

US 2022/0362385 A1    Nov. 17, 2022

Related U.S. Application Data

(60) Continuation of application No. 16/435,306, filed on Jun. 7, 2019, now Pat. No. 11,351,262, which is a continuation of application No. 15/240,871, filed on Aug. 18, 2016, now Pat. No. 10,328,152, which is a continuation-in-part of application No. 14/275,625, filed on May 12, 2014, now abandoned, which is a division of application No. 13/526,332, filed on Jun. 18, 2012, now abandoned.

(60) Provisional application No. 61/497,869, filed on Jun. 16, 2011.

(51) Int. Cl.
*A61K 47/40* (2006.01)
*A61K 38/06* (2006.01)
*A61K 38/16* (2006.01)
*A61K 9/00* (2006.01)
*A61K 31/375* (2006.01)
*A61K 47/18* (2017.01)
*A61K 47/22* (2006.01)
*A61K 47/42* (2017.01)
*A61K 9/16* (2006.01)
*A61K 31/34* (2006.01)
*A61K 31/385* (2006.01)
*A61K 31/724* (2006.01)
*A61K 31/198* (2006.01)
*A61K 31/355* (2006.01)

(52) U.S. Cl.
CPC ............ *A61K 47/40* (2013.01); *A61K 9/0014* (2013.01); *A61K 9/1617* (2013.01); *A61K 31/198* (2013.01); *A61K 31/34* (2013.01); *A61K 31/355* (2013.01); *A61K 31/375* (2013.01); *A61K 31/385* (2013.01); *A61K 31/724* (2013.01); *A61K 38/063* (2013.01); *A61K 38/16* (2013.01); *A61K 47/186* (2013.01); *A61K 47/22* (2013.01); *A61K 47/42* (2013.01)

(58) Field of Classification Search
CPC .. A61K 9/0014; A61K 31/724; A61K 31/385; A61K 38/16; A61K 2300/00; A61K 9/1617; A61K 47/22; A61K 31/355; A61K 47/40; A61K 38/063; A61K 31/375; A61K 31/198; A61K 47/186; A61K 47/42; A61K 31/34
See application file for complete search history.

(56) References Cited

U.S. PATENT DOCUMENTS

| | | |
|---|---|---|
| 4,596,795 A | 6/1986 | Pitha |
| 1,687,738 A | 8/1987 | Ginnaga et al. |
| 4,877,778 A | 10/1989 | Carpenter et al. |
| 5,229,370 A | 7/1993 | Ammeraal |
| 5,321,014 A | 6/1994 | Janz et al. |
| 5,324,718 A | 6/1994 | Loftsson |
| 5,376,632 A | 12/1994 | Konings et al. |
| 5,376,641 A | 12/1994 | Ammeraal |
| 5,407,667 A | 4/1995 | Matsuura et al. |
| 5,565,317 A | 10/1996 | Dohi et al. |
| 5,856,359 A | 1/1999 | Fischer et al. |
| 5,942,501 A | 8/1999 | Hayward et al. |
| 6,265,450 B1 | 7/2001 | Asami et al. |
| 6,573,299 B1 | 6/2003 | Petrus |
| 6,884,790 B2 | 4/2005 | Pitha |
| 6,969,706 B1 | 11/2005 | Chang et al. |
| 7,435,720 B2 | 10/2008 | Quay et al. |
| 2002/0010154 A1 | 1/2002 | Uchiyama et al. |
| 2002/0025946 A1 | 2/2002 | Buchanan et al. |
| 2003/0130231 A1 | 7/2003 | Regiert et al. |
| 2003/0161871 A1 | 8/2003 | Hird et al. |
| 2004/0067890 A1 | 4/2004 | Gupta |

(Continued)

FOREIGN PATENT DOCUMENTS

| | | |
|---|---|---|
| CN | 102100904 A | 6/2011 |
| CN | 106074206 A | 11/2016 |

(Continued)

OTHER PUBLICATIONS

Lopedota et al., "The use of Eudragit RS 100/cyclodextrin nanoparticles for the transmucosal administration of glutathione", European Journal of Pharmaceutics and Biopharmaceutics, Mar. 10, 2009, pp. 509-520.

(Continued)

*Primary Examiner* — Satyendra K Singh
(74) *Attorney, Agent, or Firm* — Knobbe, Martens, Olson & Bear, LLP

(57) ABSTRACT

A method of treatment is disclosed, comprising administering a composition of Cyclodextrin and reduced, nanonized L-Glutathione to a patient in need of treatment, wherein the L-Glutathione molecule is non-acetylated, non-Esterified, and non-fatty acid attached.

15 Claims, 14 Drawing Sheets

(56) References Cited

U.S. PATENT DOCUMENTS

| | | |
|---|---|---|
| 2005/0187188 A1 | 8/2005 | Stein et al. |
| 2005/0287205 A1 | 12/2005 | Wang et al. |
| 2006/0120967 A1 | 6/2006 | Namburi et al. |
| 2006/0172005 A1 | 8/2006 | Hara et al. |
| 2006/0246140 A1 | 11/2006 | Lochard et al. |
| 2007/0161563 A1 | 7/2007 | Quay et al. |
| 2007/0202051 A1 | 8/2007 | Schuschnig |
| 2007/0243180 A1 | 10/2007 | Tanaka et al. |
| 2008/0026074 A1 | 1/2008 | Sivak et al. |
| 2008/0145411 A1 | 6/2008 | Shinagawa et al. |
| 2009/0053378 A1 | 2/2009 | Prakash et al. |
| 2009/0054520 A1 | 2/2009 | Surburg et al. |
| 2009/0130218 A1 | 5/2009 | Skiba et al. |
| 2009/0246186 A1 | 10/2009 | Shinagawa et al. |
| 2009/0270507 A1 | 10/2009 | Pierres et al. |
| 2010/0021398 A1 | 1/2010 | Skinner |
| 2010/0130912 A1 | 5/2010 | Berenson |
| 2010/0184688 A1 | 7/2010 | Quay et al. |
| 2011/0015372 A1 | 1/2011 | Skinner |
| 2011/0034564 A1 | 2/2011 | Parkkinen |
| 2012/0321603 A1 | 12/2012 | Patel et al. |
| 2016/0228490 A1 | 8/2016 | Arnold et al. |
| 2017/0095561 A1 | 4/2017 | Patel et al. |

FOREIGN PATENT DOCUMENTS

| | | |
|---|---|---|
| CN | 107812179 A | 3/2018 |
| JP | 6463342 | 3/1989 |
| KR | 930010889 | 11/1993 |
| WO | WO 95/13047 | 5/1995 |
| WO | WO 1998/030228 A1 | 7/1998 |
| WO | WO 2008/087034 | 7/2008 |

OTHER PUBLICATIONS

Challa et al., "Cyclodextrins in Drug Delivery: An Updated Review", MPS PharmSciTech Oct. 14, 2005; 6 (2) Article 43 {http://www.aapspharmscitech.org), pp. E329-E357.

Garcia-Fuentes et al., "Protection of the peptide glutathione by complex formation with a-cyclodextrin: NMR spectroscopic analysis and stability study", European Journal of Pharmaceutics and Biopharmaceutics, Jun. 2, 2006, pp. 146-153.

Buschmann et al., "Applicationso f cyclodextrinsin cosmeticp roducts: A review", Jan. 31, 2002, pp. 185-191.

Harada, et al., (Derwent Abstract in English)—JP-01063342 A, published on Mar. 9, 1989, Stabilising glutathione-containing compositions, pp. 1-2.

PCT/US2012/042997, International Search Report and Written Opinion, dated Jan. 30, 2013.

Negi et al. "Preparation of gamma cyclodextrin stabilized solid lipid nanoparticles (SLNS) using stearic acid-gamma-cyclodextrin inclusion complex", J. Incl. Phenom. Macrocycl. Chem., 2014, vol. 80, pp. 359-368. (Year: 2014).

International Search Report and Written Opinion dated Aug. 13, 2021 for Application No. PCT/US2021/033456.

Horowitz, R.I., et al., "Efficacy of glutathione therapy in relieving dyspnea associated with COVID-19 pneumonia: A report of 2 cases", Respiratory Medicine Case Reports (2020) vol. 30, Article 101063, pp. 1-7 (Epub Apr. 21, 2020).

| Aracelli ||
| Time samples were drawn min | GHS level micro mole/L |
| --- | --- |
| 0 | 889 |
| 20 | 947 |
| 40 | 995 |
| 60 | 1054 |

| Analysis | Claim |
|---|---|
| Glutathione Reduced | 173 mg/ml |
| Glutathione Oxidized | 16.3 mg/ml |

Method: ALC190A For Glutathione Oxidized, Glutathione Reduced

*FIG. 3*

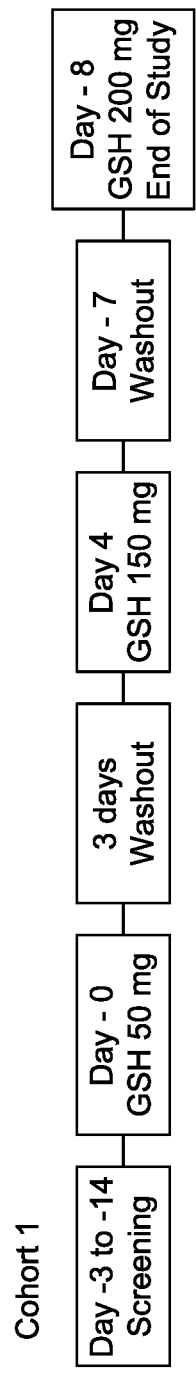
FIG. 5A  Study Design Flow Chart
Cohort 1
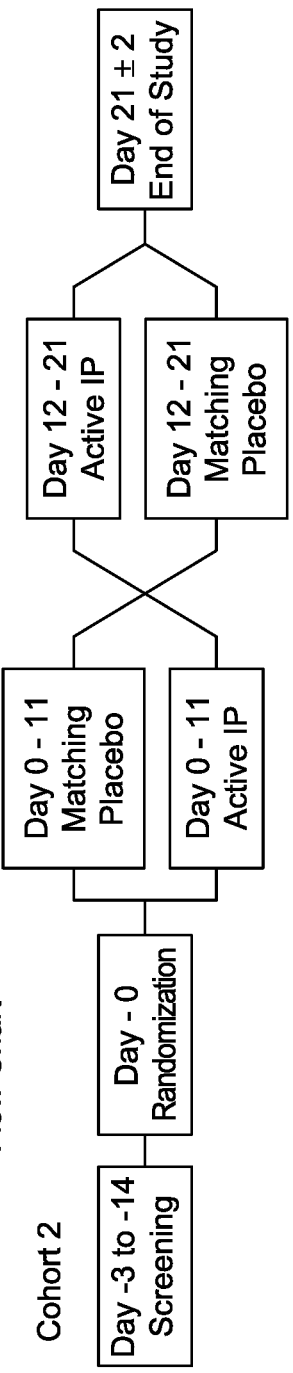
FIG. 5B  Study Design Flow Chart
Cohort 2

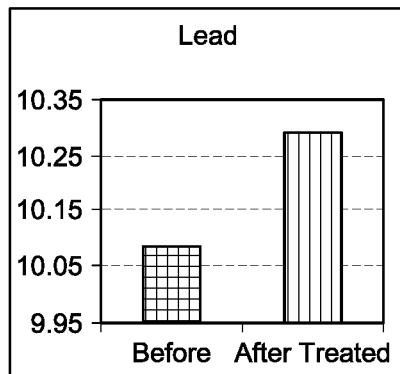
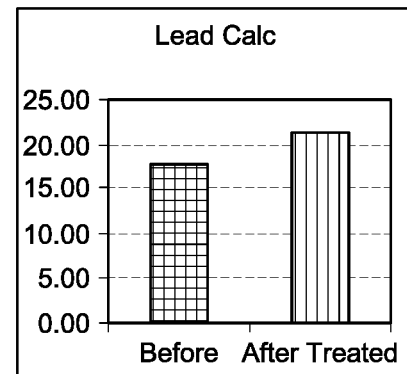
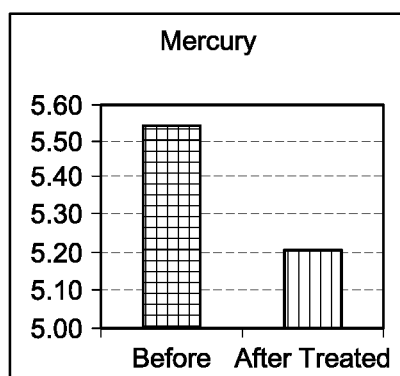
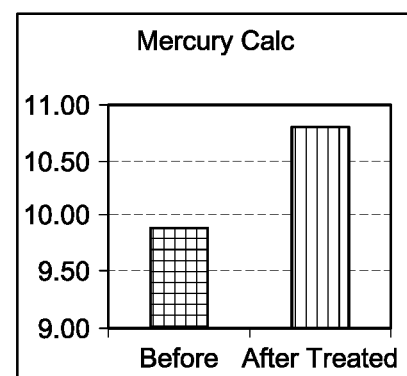
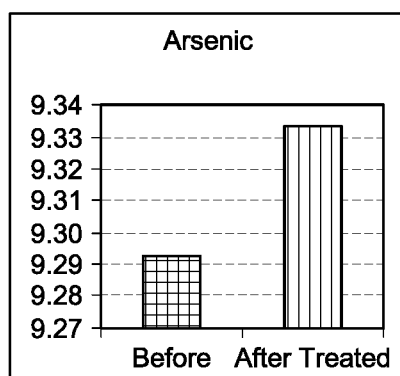
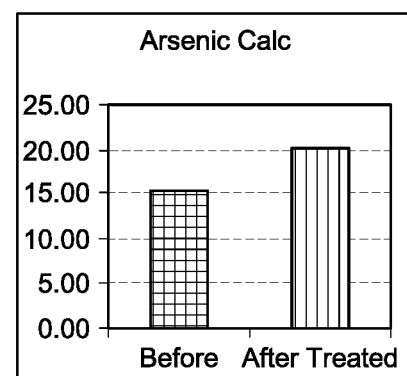
FIG. 10

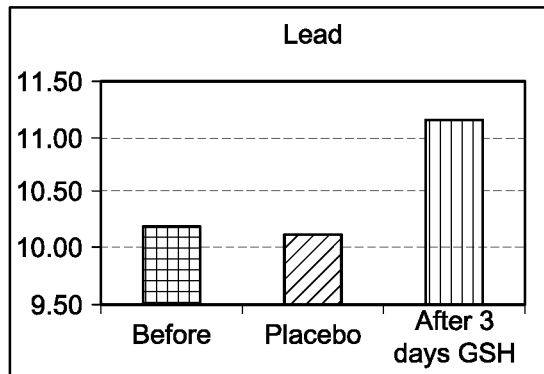
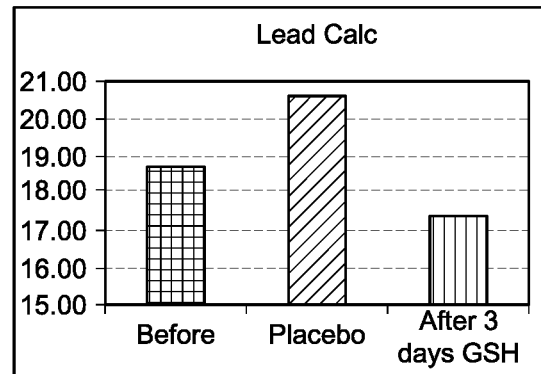
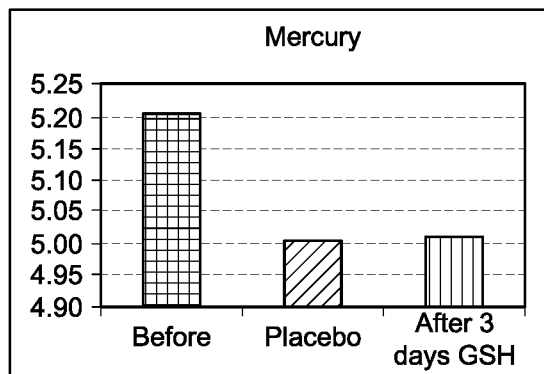
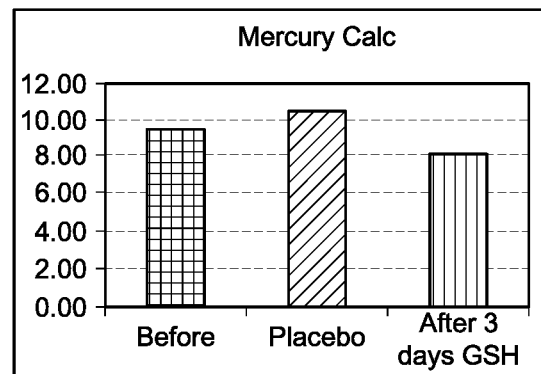
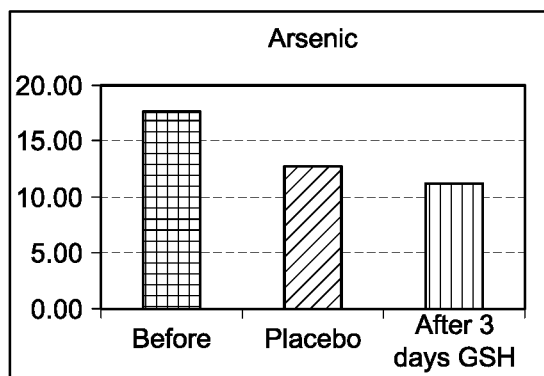
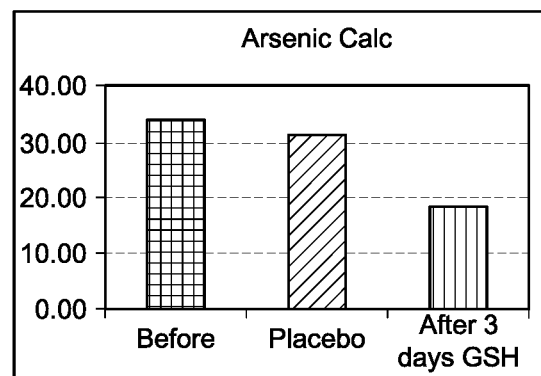
FIG. 12

| INGREDIENTS | QUANTITY USED |
|---|---|
| GLUTATHIONE (L) REDUCED | 200 GMS |
| WATER STERILE LIQUID | 1000 ML |
| ASCORBIC ACID USP FINE POWDER | 40 GMS |
| BENZALKONIUM CHLORIDE 50% NF SOLUTION | 0.4 ML |
| CYCLODEXTRIN GAMMA | 245 GMS |
| SODIUM HYDROXIDE SATURATED SOLUTION | 45 ML |

FIG. 14

METHOD FOR STABILIZATION AND DELIVERY OF THERAPEUTIC MOLECULES

CROSS-REFERENCES TO RELATED APPLICATIONS

This application is a continuation of U.S. patent application Ser. No. 16/435,306, filed Jun. 7, 2019, which is a continuation of U.S. patent application Ser. No. 15/240,871, filed Aug. 18, 2016, which is a continuation-in-part of U.S. patent application Ser. No. 14/275,625, filed May 12, 2014, which is a divisional of U.S. patent application Ser. No. 13/526,332, filed Jun. 18, 2012, which claims priority to U.S. Provisional Patent Application No. 61/497,869, filed on Jun. 16, 2011, all of which are incorporated herein by reference in their entireties.

FIELD

The subject matter disclosed herein relates to molecular stabilization and delivery using Cyclodextrin and more particularly relates to stabilization and delivery of Glutathione and other therapeutic or bio-enhancing molecules.

BACKGROUND

Glutathione (c-glutamylcysteinylglycine, GSH) is the major thiolated small peptide present in living cells. Due to its reducing and nucleophilic properties, GSH acts as a redox buffer, thus preventing oxidative damage. Glutathione depletion has been observed in a number of disease conditions including lung and neurological diseases such as acute respiratory-disease, and Parkinson's-disease, respectively. Glutathione is indicated in the treatment of alcohol and drug poisoning, as well as for protection against toxicity induced by cytotoxic chemotherapy and radiation trauma and also in the treatment of AIDS-associated cachexia. However, due to the chemical and enzymatic degradation of the peptide in the jejunum, Glutathione is typically administered intravenously. Additionally, the thiol group of the cysteine moiety in Glutathione is susceptible to enzymatic (c-glutamyl-transpeptidase) and non-enzymatic pH-dependent oxidation, leading to rapid degradation into non-active products. Therefore, the development of a technological approach that non-toxically stabilizes the Glutathione molecule against oxidation and bypasses the digestive system would increase the use and clinical value of Glutathione. This technology would also enhance the use of other therapeutic and bio-enhancing molecules.

SUMMARY

From the foregoing discussion, it should be apparent that a need exists for a composition and method that non-toxically stabilizes a therapeutic or bio-enhancing molecule including but not limited to Glutatione. Beneficially, such a composition and method would provide transdermal, transmucosal, or other non-digestive and non-intravenous delivery. Accordingly, the composition and method provided herein have been developed to provide for stabilization and delivery of Glutathione and other natural molecules.

Provided herein is a treatment method comprising administering to a patient in need of treatment a composition comprising gamma Cyclodextrin, reduced, nanonized L-Glutathione, and an antioxidant, wherein the reduced L-Glutathione is non-acetylated, non-Esterified, and non-fatty acid attached.

In certain embodiments the Cyclodextrin is gamma Cyclodextrin. The natural molecule sometimes comprises one or more of L-Glutathione and nanonized reduced Glutathione (RealGSH™). In some embodiments the natural molecule comprises at least one of a protein, a fragment thereof, and a polypeptide.

In some embodiments the natural molecule comprises at least one of nucleic acid and fragment thereof. The fragment thereof may comprise at least one of oligonucleotide, DNA, and RNA.

In certain embodiments the antioxidant comprises at least one of alpha-Lipoic Acid, Ascorbic acid, Uric acid, beta-Carotene, alpha-Tocopherol, dimethylethanolamine (DMAE), CoEnzyme Q10, vitamin E, Carnosine, colloidal silver, and the enzymes catalase, superoxide dismutase, and peroxidase. The carrier sometimes comprises one or more of a liquid, a spray, an aerosol, a cream, a tablet, a capsule, a suppository, a lotion, an aqueous solution, a powder, a paste, an ointment, a jelly, a wax, an oil, a lipid, a lipid (cationic or anionic) containing vesicle (such as Lipofectin™), a DNA conjugate, an anhydrous absorption paste, an oil-in-water and water-in-oil emulsion, an emulsion a carbowax (polyethylene glycols of various molecular weights), a semi-solid gel, and a semi-solid mixture containing carbowax.

In some embodiments of the method herein provided the composition is formulated for sustained delivery. The composition is sometimes applied to one or more of the skin, mucosa, nose, eye, and lung.

Further provided herein is a method of treatment comprising, in some embodiments, administering a composition of gamma Cyclodextrin, nanonized, reduced Glutathione that is non-acetylated, non-Esterified, and non-fatty acid attached, and an antioxidant to a patient to treat a specific condition. The patient may be an animal selected from the group consisting of mammal, bird, reptile, amphibian, and fish. The mammal is sometimes a human.

In certain embodiments the condition to be treated comprises one or more of alcohol or drug poisoning, intoxication, alcohol "hang over," toxicity induced by cytotoxic chemotherapy, radiation trauma, AIDS-associated cachexia, HIV Aids, shingles, frostbite, heavy metal poisoning, burns including laser burn, sun burn, traumatic burn, thermal burn, chemical burn, acne, pressure sore, autism, scar tissue, Parkinson's disease, hepatitis B, hepatitis C, upper respiratory virus infections (cold), cystic fibrosis, insect bites (mosquito, spider, etc.), pain in limbs, neuropathy, Reflex Sympathetic Dystrophy (RSD), rheumatoid arthritis, multiple sclerosis, osteoarthritis, psoriasis, psoriatic arthritis, jet lag, kidney disease (CRF CKD), akathisia, and tardive dyskinesia.

In various embodiments the condition to be treated comprises one or more of obesity, decreased immunity, inflammation, angina, heart disease, and cardiac reperfusion injury, lung-and-neurological-diseases such as acute respiratory-disease, emphysema, pulmonary fibrosis and associated muscle wasting, asthma, migraine headaches; Parkinson's-disease, herpes zoster, HSV, hepatitis B&C, and influenza, fibromyalgia; osteoporosis/osteomalacia, cancer including but not limited to brain, head and neck, thyroid, lung, esophagus, stomach, intestine, liver, pancreas, kidney uterine, ovarian, prostate, leukemia (acute and chronic), lymphoma, multiple myeloma, and others, systemic sclerosis (scleroderma) syndrome, sepsis, trauma, wrinkles, sagging skin, acne, atopic dermatitis and eczema, athletic overtraining and muscle fatigue; schizophrenia, bipolar disorder, major depressive disorder, dementia, autism, Attention Deficit Hyperactive Disorder (ADHD); overdose of acetaminophen, low energy, drug toxicity, eye problems including cataracts, glaucoma, macular degeneration, macular dystrophy, diabetic retinopathy, decreased visual acuity, diabetic retinopathy, and contrast sensitivity; biomolecule imbalances resulting from traumatic head injury or other causes, and infertility in men and women.

Also provided herein is a method for stabilizing reduced L-Glutathion comprising bringing reduced L-Glutathione and an antioxidant in contact with solubilized Cyclodextrin in a polar solution to form a complex of reduced L-Glutathione and antioxidant compound and Cyclodex, adjusting the pH to a range compatible with preserving the complex, and exposing the complex to Ultrasonic waves sufficient to create complex nanoparticles of sizes in the range of from 2 nanometers to 200 nanometers. The Cyclodextrin is sometimes gamma-Cyclodextrin. In some embodiments the polar solution is aqueous. The polar solution of a reaction mixture may comprise ascorbic acid and Benzalkonium chloride, and the reaction mixture may be capped under vacuum after mixing at a pH in the range of 3.0 to 7.0. The antioxidant is sometimes a soluble compound having antioxidant activity and comprising a mixture of two or more of ascorbic acid, ascorbic acid derivatives, L-Cysteine, N-Acetyl Cysteine, L-Carnitine, Acetyl-L-carnitine, Riboflavine and Curcuminoids. The antioxidant may be in the range of 0.001 mole and 100 moles per mole of reduced L-Glutathione and in certain embodiments the antioxidant is not less than 0.01 mole and not more than 10 moles per mole of reduced L-Glutathione.

Further provided herein is an embodiment of a kit for topical application, the kit comprising a complex of gamma Cyclodextrin and reduced, nanonized, L-Glutathione, which is non acetylated, non-Esterified, and non-fatty acid attached, a container for dispensing the composition, a composition applicator and one or more of instructions for use.

Reference throughout this specification to "some embodiments," "certain embodiments," "various embodiments" or similar language means that a particular feature, structure, or characteristic described in connection with the embodiment is included in at least one embodiment. Thus, appearances of the phrases "in some embodiments," "in certain embodiments," "in various embodiments," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, structures, or characteristics of the embodiments may be combined in any suitable manner. One skilled in the relevant art will recognize, however, that embodiments may be practiced without one or more of the specific details, or with other methods, components, materials, and so forth. Rather, language referring to the features and advantages is understood to mean that a specific feature, advantage, or characteristic is included in at least one embodiment. Thus, discussion of the features and advantages, and similar language, throughout this specification may, but does not necessarily, refer to the same embodiment. In other instances, well-known protocols, reagents, materials, or operations are not shown or described in detail to avoid obscuring aspects of an embodiment.

These features and advantages of the embodiments will become more fully apparent from the following description and appended claims, or may be learned by the practice of embodiments as set forth hereinafter.

BRIEF DESCRIPTION OF THE DRAWINGS

FIG. 1B is a graph depicting venous blood levels of GSH of a male 65 years old after administering 200 mg of gamma-Cyclodextrin/GSH complex on forearm. Samples were drawn as indicated at time in FIG. 1A.

FIG. 2B is a graph depicting venous blood level of GSH of a female about 28 years old after administering 200 mg of gamma-Cyclodextrin/GSH complex on forearm. Samples were drawn as indicated at time in FIG. 2A.

FIG. 3 depicts the results of an independent laboratory analysis of the raw topical stabilized GSH, without preservatives, as provided herein. The gel is the result of stabilizing the highly reactive cysteine moiety of GSH in a gamma-Cyclodextrin ring using high energy waves in an oxygen environment. The samples were sent via U.S. Mail in test tubes with full exposure to atmospheric oxygen.

FIG. 5A/B depicts the study design for evaluation of the safety and efficacy of topical Glutathione stabilized in a gamma-Cyclodextrin ring structure (Example 11).

FIG. 6A is a graph depicting a dose-based comparison of glutathione absorption at doses of 50 mg/ml, 100 mg/ml and 200 mg/ml at incremental times from pre-dose to 180 minutes post-dose as indicated in FIG. 6B (Example 9).

FIG. 7A is a graph depicting a dose-based comparison of blood levels of superoxide dismutase at doses of 50 mg/ml, 100 mg/ml, and 200 mg/ml at incremental times from pre-dose to 180 minutes post-dose as indicated in FIG. 7B (Example 9).

FIG. 8A is a graph depicting a dose-based comparison of blood levels of glutathione peroxidase at doses of 50 mg/ml, 100 mg/ml, and 200 mg/mg at incremental times from pre-dose to 180 minutes post-dose as indicated in FIG. 8B (Example 9).

FIG. 9A is a graph depicting a dose-based comparison of blood levels of lipid peroxidase at doses of 50 mg/ml, 100 mg/ml, and 200 mg/mg at incremental times from pre-dose to 180 minutes post-dose as indicated in FIG. 9B (Example 9).

FIG. 10 is a series of bar graphs depicting urinary output and calculated urinary output of lead, mercury, and arsenic in 24 treated volunteers, within a 34 volunteer study, before and after treatment with GSH, as measured by Electrothermal (Flameless) AAS and Mercury Hydride procedure through Mountain Star Clinical Laboratories. (Example 10).

FIG. 12 is a series of bar graphs depicting urinary output and calculated urinary output of lead, mercury, and arsenic in a 10 volunteer placebo group, within a 34 volunteer study, before intervention, after receiving a placebo, and after treatment with GSH, as measured by Electrothermal (Flameless) AAS and Mercury Hydride procedure through Mountain Star Clinical Laboratories. (Example 10).

FIG. 14 is a reproduction of a formula worksheet for the production of a stabilized glutathione-Cyclodextrin complex (Example 1).

DETAILED DESCRIPTION

Herein provided is a composition and method of treatment for protecting and stabilizing therapeutic and bio-enhancing molecules, including Glutathione, by means of a gamma-Cyclodextrin complex. The composition comprising this complex may optionally include other molecules, for non-limiting example, antioxidants such as Alpha-Lipoic Acid, Ascorbic acid, Uric acid, Betacarotens, alphaTocopherol, DMAE and CoEnzyme Q10. The gamma-Cyclodextrin additionally facilitates transdermal and transmucosal delivery of the molecules, thus bypassing the digestive tract and eliminating the need for intravenous administration. Transdermal stabilized glutathione is a novel form of Glutathione that has been stabilized using encapsulation in gamma-Cyclodextrin ring structures that prevents oxidation of the reduced Glutathione by atmospheric oxygen.

Antioxidants

An antioxidant is a molecule capable of inhibiting the oxidation of other molecules. Oxidation is a chemical reaction that transfers electrons from a substance to an oxidizing agent. Oxidation reactions can produce free radicals. In turn, these radicals can start chain reactions. When the chain reaction occurs in a cell, it can cause damage or death. Antioxidants terminate these chain reactions by removing free radical intermediates, and inhibit other oxidation reactions. They do this by being oxidized themselves, so antioxidants are often reducing agents including thiols such as GSH, ascorbic acid, or polyphenols. Thiol groups exist at a concentration of approximately 5 mM in animal cells. Glutathione reduces disulfide bonds formed within cytoplasmic proteins to cysteines by serving as an electron donor. In the process, Glutathione is converted to its oxidized form Glutathione disulfide (GSSG).

Although oxidation reactions are crucial for life, they can also be damaging and oxidative stress appears to be an important part of many human diseases. Therefore, plants and animals maintain complex systems of multiple types of antioxidants, such as GSH, vitamin C, and vitamin E as well as enzymes such as catalase, superoxide dismutase, and various peroxidases. Low levels of antioxidants, or inhibition of the antioxidant enzymes, cause oxidative stress and may damage or kill cells.

Cyclodextrin

Cyclodextrins (sometimes called cycloamyloses) are a family of compounds made up of sugar molecules bound together in a ring (cyclic oligosaccharides) and are produced from starch by means of enzymatic conversion. Cyclodextrins are used in food, pharmaceutical, and chemical industries, as well as agriculture and environmental engineering.

Figure 4:
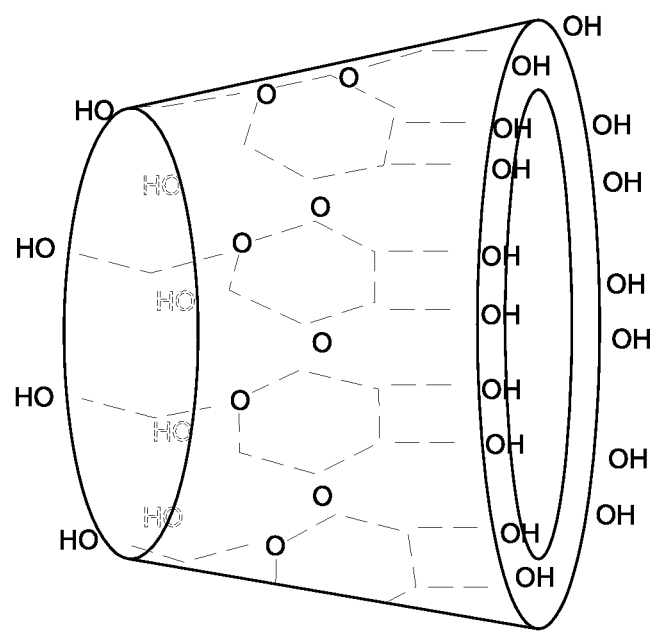
FIG. 4 depicts the toroid structure of Cyclodextrin.

Cyclodextrins are composed of 5 or more (1,4)-linked α-D-glucopyranose units. Topologically, Cyclodextrins form a torus with a hydrophobic interior and a hydrophilic exterior. Typical Cyclodextrins contain a number of glucose monomers ranging from six to eight units in a ring, creating a cone shape. Alpha-Cyclodextrin is a six membered sugar ring molecule, beta-Cyclodextrin is a seven sugar ring molecule, and gamma-Cyclodextrin in an eight sugar ring molecule. Cyclodextrins can be topologically represented as toroids with the larger and the smaller openings of the toroid exposing to the solvent secondary and primary hydroxyl groups respectively. (See FIG. 4.) Because of this arrangement, the interior of the toroid is not hydrophobic, but considerably less hydrophilic than the aqueous environment and thus able to host other hydrophobic molecules. In contrast, the exterior is sufficiently hydrophilic to impart water solubility to Cyclodextrins (or their complexes).

This allows Cyclodextrins to act as host molecules that form inclusion complexes with hydrophobic guest molecules. Cyclodextrins are known to influence the percutaneous absorption of therapeutic agents by both a solubilizing action on the drug thus increasing its availability at the absorption site and by an interaction with the free lipids present in the stratum corneum resulting in improvement of transdermal penetration of therapeutic agents.

The formation of the inclusion compounds greatly modifies the physical and chemical properties of the guest molecule, mostly in terms of water solubility. Thus, inclusion compounds of Cyclodextrins with hydrophobic molecules are able to penetrate body tissues, and can be used to release biologically active compounds under specific conditions. The mechanism of controlled degradation of such complexes is sometimes based on pH change of solutions, leading to the cleavage of hydrogen or ionic bonds between the host and the guest molecules. Alternative means for the disruption of the complexes may involve heating or the action of enzymes able to cleave α-1,4 linkages between glucose monomers.

In Cyclodextrin inclusion one or more guest molecule interacts with the cavity of a Cyclodextrin molecule to form a stable association. Molecules or functional groups of molecules that are less hydrophilic than water can be included in the Cyclodextrin cavity in the presence of water. The "guest molecules" may fit, at least partly, into the Cyclodextrin cavity. The cavity sizes as well as possible chemical modifications determine the affinity of Cyclodextrins to the various molecules. In the case of some low molecular weight molecules, more than one guest molecule may fit into the cavity. Conversely, some high molecular weight molecules may bind more than one Cyclodextrin molecule. Therefore a 1:1 molar ratio is not always achieved. Gamma-Cyclodextrin, as provided herein, exhibits compatibility with Glutathione, and protects the Glutathione molecule sufficiently to usefully extend the Glutathione half-life in the bloodstream.

In the solid state the guest molecule is molecularly dispersed in the Cyclodextrin matrix, even with gaseous guest molecules. Thus, the guest molecule is effectively protected against any type of reaction, except with Cyclodextrin's hydroxyls. In aqueous solution the concentration of a poorly soluble guest molecule in the dissolved phase increases significantly. Reactivity of the guest molecule decreases in most cases.

Cyclodextrins are able to form inclusion complexes with a broad range of hydrophobic molecules, with the larger gamma-Cyclodextrin accepting more bulky compounds. As provided herein, Cyclodextrins and gamma-Cyclodextrin in particular can form compounds with peptides, polypeptides, proteins, amino acids, nucleic acids, polynucleotides, DNA, and RNA Anti-oxidants such as ascorbic acid, carnosine, alpha-Lipoic Acid, DMAE, CoEnzuyme Q10 and other molecules such as colloidal silver may enhance the protective function of the complex and perform various other functions.

Cyclodextrin complexation of a drug may increase drug stability, sustaining the release and minimizing the photodegradation of a complexed drug. Cyclodextrin complexation has utility in improving the chemical, physical and thermal stability of drugs. Chemical reactions are necessary in order for an active molecule to degrade upon exposure to oxygen, water, radiation or heat. When a molecule is entrapped within the Cyclodextrin cavity, it is difficult for the reactants to diffuse into the cavity and react with the protected guest.

The stabilized Cyclodextrin-Glutthione compound comes in the form of a gel that is applied topically. The Cyclodextrin ring structures are broken down by naturally occurring enzymes on the skin and the reduced glutathione is absorbed transdermally and enters the bloodstream.

Glutathione

Glutathione (GSH) as provided herein is natural, non-esterified, non-acetylated, and non-fatty acid attached, fostering high bioavailability. Gluthatione is a tripeptide that contains an unusual peptide linkage between the amine group of cysteine and the carboxyl group of the glutamate side-chain. It is an antioxidant, preventing damage to various cellular components caused by reactive oxygen species such as free radicals and peroxides. Glutathione is the most abundant low molecular weight thioltripeptide synthesized in cells and helps to maintain other antioxidants (such as Vitamin C) in the active reduced form. Clinical use of Glutathione in medicine has been limited because of its unstable nature due to the cysteine moiety of the Gluta-thione. Thus, if Glutathione is given intravenously, much of the Glutathione is oxidized into GSSG in the IV-bag during storage, transport or while being infused. Nebulized forms have also been used but the smell and taste result in poor patient compliance and it is counterintuitive to suggest that aerosolizing a compound that is highly reactive in the presence of atmospheric oxygen is an effective strategy.

In vivo, Glutathione is found almost exclusively in its reduced form, since the enzyme that reverts it from its oxidized form, Glutathione reductase, is constitutively active and inducible upon oxidative stress. In fact, the ratio of reduced Gluathione to oxidized Glutathione within cells is often used as a measure of cellular toxicity. Glutathione helps prevent damage to cells by neutralizing harmful molecules generated during energy production. Glutathione also plays a role in processing medications and cancer-causing compounds (carcinogens), and building DNA, proteins, and other important cellular components.

Glutathione is known as a substrate in both conjugation reactions and reduction reactions-catalyzed by glutathione S-transferase enzymes-in cytosol, microsomes, and mitochondria. However, it is also capable of participating m non-enzymatic conjugation with some chemicals. Gluta-thione participates in leukotriene synthesis and is a cofactor for the enzyme glutathione peroxidase. It is also important as a hydrophilic molecule that is added to lipophilic toxins and waste in the liver during biotransformation before they can become part of the bile. Glutathione also assists in the detoxification of methylglyoxal, a toxin produced as a by-product of metabolism.

Low Glutathione is strongly implicated in wasting and negative nitrogen balance, as seen in cancer, AIDS, sepsis, trauma, burns and even athletic overtraining. Glutathione supplementation can oppose this process, and in AIDS, for example, result in improved survival rates. Schizophrenia and bipolar disorder are associated with lowered Glutathione. Accruing data suggest that oxidative stress may be a factor underlying the pathophysiology of bipolar disorder (BD), major depressive disorder (MDD), and schizophrenia (SCZ). Glutathione is the major free radical scavenger in the brain. Diminished Glutathione levels elevate cellular vulnerability towards oxidative stress; characterized by accumulating reactive oxygen species. Replenishment of Glutathione using N-acetyl cysteine has been shown to reduce symptoms of these disorders.

Glutathione is an antidote to overdose in the case of N-acetyl-p-benzoquinone imine (NAPQI), the reactive cytochrome P450-reactive metabolite formed by paracetamol (known in the U.S. as acetaminophen), that becomes toxic when Glutathione is depleted by an overdose of acetaminophen. Glutathione conjugates to NAPQI and helps to detoxify it. In this capacity, it protects cellular protein thiol groups, which would otherwise become covalently modified; when all Glutathione has been spent, NAPQI begins to react with the cellular proteins, killing the cells in the process.

Preliminary results on isolated cells indicate Glutathione changes the level of reactive oxygen, which may reduce cancer development. Additional evidence indicates that adequate levels of Glutathione help to control the level of Tumor necrosis factor (TNF)—a group of cytokines that can cause cell death. However, once a cancer has already developed, elevated levels of GSH in tumor cells confers resistance to a number of chemotherapeutic drugs, and thus protects cancerous cells in bone marrow, breast, colon, larynx, and lung cancers.

Excess glutamate at synapses, which may be released in conditions such as traumatic brain injury, can prevent the uptake of cysteine, a necessary building-block of Gluta-thione. Without the protection from oxidative injury afforded by Glutathione, cells may be damaged or killed.

Raising Glutathione levels through direct supplementation of Glutathione is difficult. Research suggests that Glutathione taken orally is broken down by digestive enzymes and not well absorbed across the gastrointestinal tract. Additionally, natural GSH can be quite rapidly oxidized upon exposure to air. Some attempts have been made to stabilize Glutathione by acetylating or esterifying the Glutathione thiol group.

The composition provided herein obviates the necessity of acetylating, esterifying, or otherwise modifying the Gluta-thione. The disclosed composition comprises a complex of reduced L-Glutathione and gamma-Cyclodextrin, as discussed below, which protects the Glutathione from degradation and oxidation without the necessity of altering the natural Glutathione molecule.

Nanonized Glutathione Cyclodextrin Complex

Nanonization of a pH stabilized Glutathione Cyclodextrin complex may facilitate rapid absorption into the bloodstream as discussed below. In some embodiments sodium hydroxide, hydrochloric acid or other acid is added to the stabilized Glutathione, antioxidant, and Gamma Cyclodextrine to adjust the pH of the solution. In various embodiments the pH is adjusted to a pH of not less than 4.00 and not more than 7.8. In certain embodiments the adjusted pH is not less than 5.00 and not more than 7.2. The solution may be nanonized using Ultrasonic waves as known in the art in the range of about 100 Watts. The Ultrasonic waves are sometimes applied for not less than 1 minute and not more than 10 minutes. In certain embodiments the Ultrasonic waves are applied for not less than 3 minutes and not more than 6 minutes.

The size of the resulting nanoparticles may be in the range of between 2 nanometers and 200 nanometers. In certain embodiments the nanoparticles have a size in the range of 2 to 20 nanometers, 20 to 40 nanometers, 40 to 60 nanometers, 60 to 80 nanometers, 80 to 100 nanometers, 100 to 120 nanometers, 120 to 140 nanometers, 140 to 160 nanometers, 160 to 180 nanometers, and 180 to 200 nanometers. In some embodiments the nanoparticles may be of mixed sizes.

Therapeutic Administration and Formulations

The composition provided herein may be formulated as a liquid, cream, solid, lotion, oil, emulsion, spray, aerosol, dissolving strip, bolus, suppository, tablet, capsule, or other formulation using compounding and other methods known in the art. In certain embodiments a guest molecule such as gamma-Cyclodextrin and GSH are combined in an aqueous solution comprising ascorbic acid and Benzalkonium chloride, and capped under vacuum after mixing at a pH of between 3.0 and 7.0. In some embodiments the pH is 5.5. In certain embodiments the pH is from 3.0 to 4.0, from 4.0 to 5.0, from 5.0 to 6.0, or from 6.0 to 7.0.

The percentage of Cyclodextrin may be from 1% to 27%. The percentage of Cyclodextrin may sometimes be from 1% to 5%, from 5% to 10%, from 10% to 15%, from 15% to 20%, from 20% to 25% and from 25% to 30%. The percentage of Glutathione or other guest molecule may be from 0.1% to 80%. In certain embodiments the percentage of Glutathione or other guest molecule is from 0.1% to 1%, from 1% to 5%, from 5% to 10%, from 10% to 15%, from 15% to 20%, from 20% to 30%, from 30% to 40%, from 40% to 50%, from 50% to 60%, from 60% to 70%, from 70% to 80%, from 80% to 85%, from 85% to 90%, and from 90 to 95%.

In some embodiments Cyclodextrin is 0.116 M. In various embodiments Glutathione is 3.1 M. The molar ratio of Glutathione to Cyclodextrin is sometimes 26 to 1. The molar ratio of GSH to Cyclodextrin may be between 1 to 15 or less and 30 to 1 or more. By way of non-limiting example, the molar ratio of Glutathione or other guest molecule to Cyclodextrin may be: 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, 1 to 2, and 1 to 1, or any fraction of the foregoing ratios. In certain embodiments the molar ratio of GSH or other guest molecule to Cyclodextrin is 1.1 to 1, 1.2 to 1, 1.3 to 1, 1.4 to 1, 1.5 to 1, 1.6 to 1, 1.7 to 1, 1.8 to 1, 1.9 to 1, 2 to 1, 3 to 1, 4 to 1, 5 to 1, 6 to 1, 7 to 1, 8 to 1, 9 to 1, 10 to 1, 11 to 1, 12 to 1, 13 to 1, 14, to, 15 to 1, 16 to 1, 17 to 1, 18 to 1, 19 to 1, 20 to 1, 21 to 1, 22 to 1, 23 to 1, 24 to 1, 25 to 1, 26 to 1, 27 to 1, 28 to 1, 29 to 1, and 30 to 1, or any fraction of the foregoing ratios. In certain embodiments the concentration of Glutathione is 950 mg/ml. In various embodiments the concentration of Cyclodextrin 150 mg/ml. The Cyclodextrin as provided above is sometimes gamma-Cyclodextrin. In some embodiments the combined concentration percentage is 95% GSH in 15% gamma-Cyclodextrin.

Various natural molecules may be combined with Cyclodextrin m a similar fashion to form inclusion complexes. In certain embodiments antioxidants and other molecules may be added, including but not limited to Ascorbic acid, Alpha-Lipoic Acid, Uric acid, alpha Tocopherols, beta Carotenes or any other antioxidant molecules.

Specifically the composition of this invention which contains a reduced L-Glutathione in a stabilizing solution which may contain an antioxidant. The antioxidant may be any soluble compound having antioxidant activity which may be mixtures of two or more of ascorbic acid, ascorbic acid derivatives, L-Cysteine, N-Acetyl Cysteine, L-Carnitine, Acetyl-L-carnitine, Riboflavine and Curcuminoids. In some embodiments the antioxidant is not less than 0.001 mole and not more than 100 moles per mole of reduced L-Glutathione, and may be not less than 0.01 mole and not more than 10 moles of reduced L-Glutathione.

A method for solubilizing and stabilizing is described. The method comprising bringing reduced L-Glutathione with another compound of antioxidant on contact with solubilized gamma-Cyclodextrin in a polar solution preferably aqueous. After such mixing a complex of reduced L-Glutathione and antioxidant compound and gamma-Cyclodextrin is formed.

The composition and method provided herein may be employed to treat a variety of conditions including without limitation: alcohol or drug poisoning, intoxication, alcohol "hang over," toxicity induced by cytotoxic chemotherapy, radiation trauma, AIDS-associated cachexia, HIV Aids, shingles, frostbite, heavy metal poisoning, bums including laser bum, sun bum, traumatic bum, thermal bum, chemical bum, acne, pressure sore, autism, scar tissue, Parkinson's disease, hepatitis B, hepatitis C, upper respiratory virus infections (cold), cystic fibrosis, acne, insect bites (mosquito, spider, etc), pain in limbs, neuropathy, Reflex Sympathetic Dystrophy (RSD), rheumatoid arthritis, multiple sclerosis, osteoarthritis, psoriasis, psoriatic arthritis, jet lag, kidney disease (CRF, CKD), and akathisia, tardive dyskinesia, obesity, decreased immunity, inflammation, angina, heart disease, and cardiac reperfusion injury, lung-and neurological-diseases such as acute respiratory-disease, emphysema, pulmonary fibrosis and associated muscle wasting, asthma; cystic fibrosis, migraine headaches; Parkinson's disease, herpes zoster, HSV, hepatitis B & C, influenza, fibromyalgia, osteoporosis/osteomalacia, systemic sclerosis (scleroderma) syndrome, sepsis, trauma, wrinkles, sagging skin, acne, atopic dermatitis and eczema, athletic overtraining and muscle fatigue; schizophrenia, bipolar disorder, major depressive disorder, dementia, autism, Attention Deficit Hyperactive Disorder (ADHD); overdose of acetaminophen, low energy, drug toxicity, eye problems including cataracts, glaucoma, macular degeneration, macular dystrophy, diabetic retinopathy, decreased visual acuity, diabetic retinopathy, and contrast sensitivity; biomolecule imbalances resulting from traumatic head injury or other causes, and infertility in men and women. The composition and method herein provided may be used to treat cancer including but not limited to brain, head and neck, thyroid, lung, esophagus, stomach, intestine, liver, pancreas, kidney uterine, ovarian, prostate, leukemia (acute and chronic), lymphoma, multiple myeloma, and others.

The composition and method may be administered under physician prescription or over the counter depending upon the natural molecule and other ingredients comprising the composition and upon the condition to be treated. The route of administration is in accord with known methods including without limitation; oral, sublingual, transdermal, cutaneous, subcutaneous, mucosal, transmucosal, inhalation, intralesional, buccal, or by sustained release systems as noted below. In some embodiments the composition as herein provided is administered via a small strip or other form of material that may dissolve in the mouth of the patient. This allows the convenience of a solid form therapy while retaining the advantages of a sublingual or mucosal delivery. The enzymes of the human mouth are capable of dissolving carbohydrates but not of breaking down peptides or proteins or many types of organic molecule. Therefore the composition may be delivered directly to the bloodstream without being exposed to digestive enzymes or crossing the intestinal barrier, and without the necessity for intravenous delivery.

An effective amount of composition to be employed therapeutically will depend, for example, upon the specific composition, therapeutic objectives, the route of administration, and the weight and condition of the patient. Accordingly, the therapist may titer the dosage and modify the route of administration as required to obtain the optimal therapeutic effect. The clinician may administer the composition until a dosage is reached that achieves the desired effect. The progress of this therapy may be monitored by conventional assays or by the assays described herein.

The therapeutic composition can be administered through the skin, mucosa, nose, eye, or lung, in formulations including a liquid, cream, lotion, oil, emulsion, gel, paste, powder, liquid or powder aerosol (lyophilized). The composition may be administered parenterally or subcutaneously as desired. The composition may be administered systemically, and may be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with physiologically acceptable carriers, excipients, or stabilizers, for example Cyclodextrin and gamma-Cyclodextrin. Such materials are non-toxic to the recipients at the dosages and concentrations employed, and may include buffers such as TRIS HCl, phosphate, citrate, acetate and other organic acid salts; antioxidants such as ascorbic acid, carnosme, alpha-Lipoic Acid; peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol.

Suitable examples of sustained-release preparations include semipermeable matrices of solid hydrophobic polymers containing the composition provided, which matrices are in the form of shaped articles, films or microcapsules. Examples of sustained-release matrices include polyesters, hydrogels (e.g., poly(2-hydroxyethyl-methacrylate), copolymers of L-glutamic acid and gamma ethyl-Lglutamate, non-degradable ethylene-vinyl acetate, degradable lactic acid-glycolic acid copolymers such as poly-D-(-)-3-hydroxybutyric acid.

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37 degree C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization may be achieved by modifying sulfhydryl residues, lyophilizing from acidic solutions, controlling moisture content, using appropriate additives, and developing specific polymer matrix compositions.

The dosage of the composition herein for a given patient will be determined by the therapist or physician taking into consideration the natural molecule comprising the composition and various factors known to modify the action of drugs including severity and type of disease, body weight, sex, diet, time and route of administration, other medications and other relevant clinical factors. Therapeutically effective dosages may be determined by either in vitro or in vivo methods.

An effective amount of the composition herein to be employed therapeutically will depend, for example, upon the therapeutic objectives, the route of administration, and the condition of the patient. Accordingly, the therapist may titer the dosage and modify the route of administration as required to obtain the optimal therapeutic effect. A daily dosage might range from about 0.001 mg/kg to up to 100 mg/kg or more, depending on the factors mentioned above. In some embodiments the dosage is 50, 100, or 200 mg of GSH administered as a topical gel. In some embodiments the dose is administered twice daily, once in the AM and once in the PM. The clinician may administer the therapeutic composition as provided herein until a dosage is reached that achieves the desired effect. The progress of this therapy may be monitored by conventional assays or as described herein.

It will be appreciated that administration of therapeutic entities in accordance with the compositions and methods herein may be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present composition, provided that the active ingredient in the formulation is not inactivated by the formulation and the formulation is physiologically compatible and tolerable with the route of administration and as known in the art.

The embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

EXAMPLES

Example 1: Preparation of Gamma Cyclodextrin & Glutathione

Final concentrations:
Glutathione 0.65 M (200 mg/ml)
Ascorbic acid 0.23 M (40 mg/ml)
Gamma Cyclodextrin 0.189 M (245 mg/ml)
Benzalkonium chloride 0.02%

1. Preparation:
1.1. Purified water 0.5 L was degassed by mixing in a capped 2 L filter Erlenmeyer flak under vacuum for 30 min with a magnetic stirrer.
1.2. Vacuum was turned off, the flask was uncapped and 200 g of L-Glutathione (Reduced form) was added into the flask. 40 g of Ascorbic acid was also added. Appropriate volume of Sodium hydroxide solution was also added to final ph oh about 5.5-6.5.
1.3. The flask was recapped, vacuum turned back on and the mixture was mixed until dissolved to a clear solution.
1.4. 150 g of Gamma-cyclodextrin was added to flask after uncapped and vacuum turned off.
   a. Purified water was added to about 1 L. The flask was recapped, vacuum turned on and the mixture was mixed until clear, about 1 h.
   b. 0.4 ml of 50% Benzalkonium chloride was added and mixed well also under vacuum.
   c. Final solution was packed into air tight dispenser. (See FIG. 14.)

Example 2: Blood Level of Glutathione

Figures 1A, 1B:
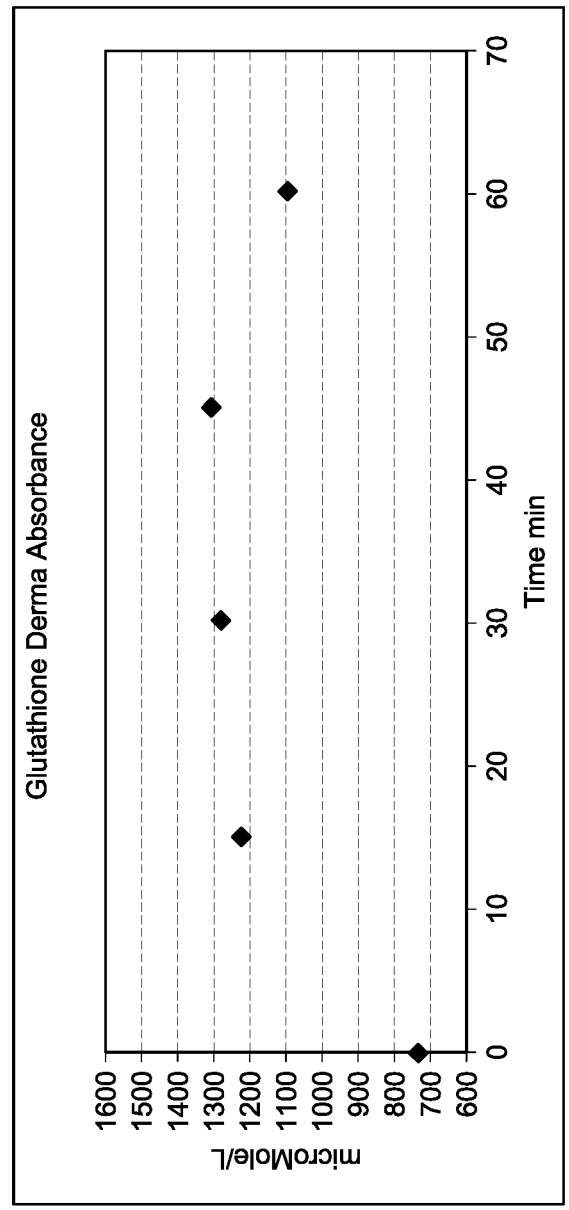
FIG. 1A-1B.
Figures 2A, 2B:
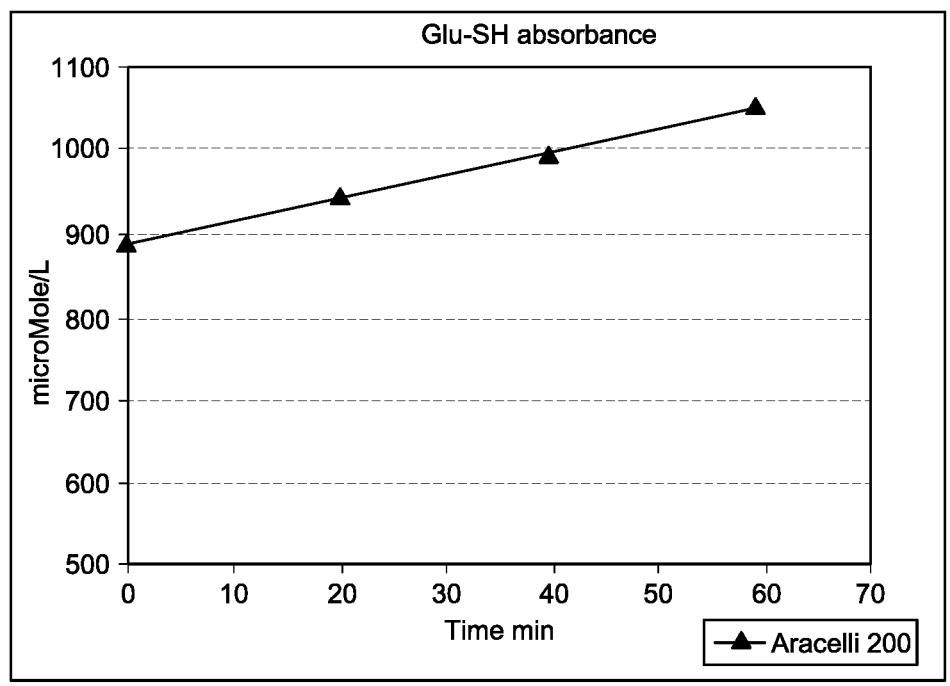
FIG. 2A-2B.

About 1 ml of 200 mg/ml GSH, 40 mg/ml Ascorbic Acid, 150 mg/ml Gamma Cyclodextrinin 0.02% Benzalkonium chloride was applied on the skin of the subject's forearm skin at time 0. A sample of 5 ml was drawn from median cubital vein of the same forearm at 15, 30, 45, and 60 min (FIG. 2A/B). Samples were kept on ice and were shipped overnight to the lab for analysis of venous levels of reduced GSH.

Example 3: Glutathione Stability

Laboratory results on raw Glutathione stabilized in the disclosed gamma-Cyclodextrin ring structure showed that the Glutathione remained 91% reduced after multiple transfers of location (FIG. 3).

Example 4: Clinical Observations on the New Topical Glutathione

Figures 6A, 6B:
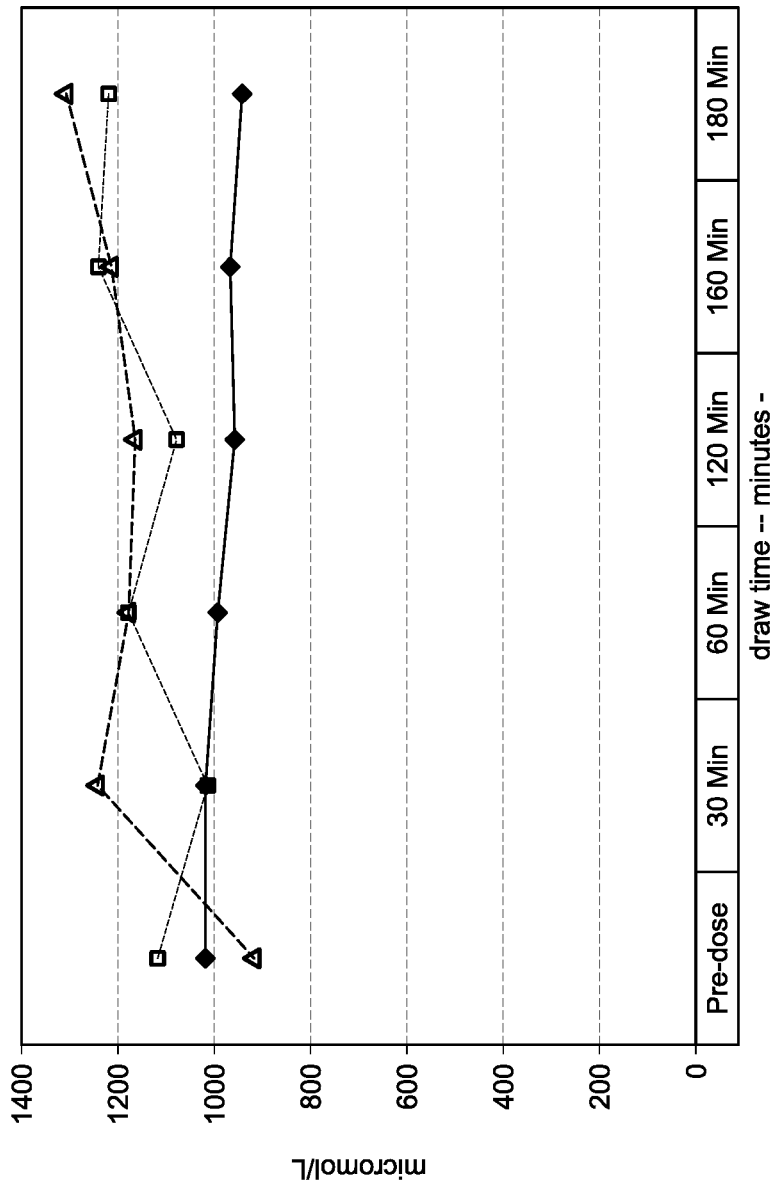
FIG. 6A-6B.
Figure 7A:
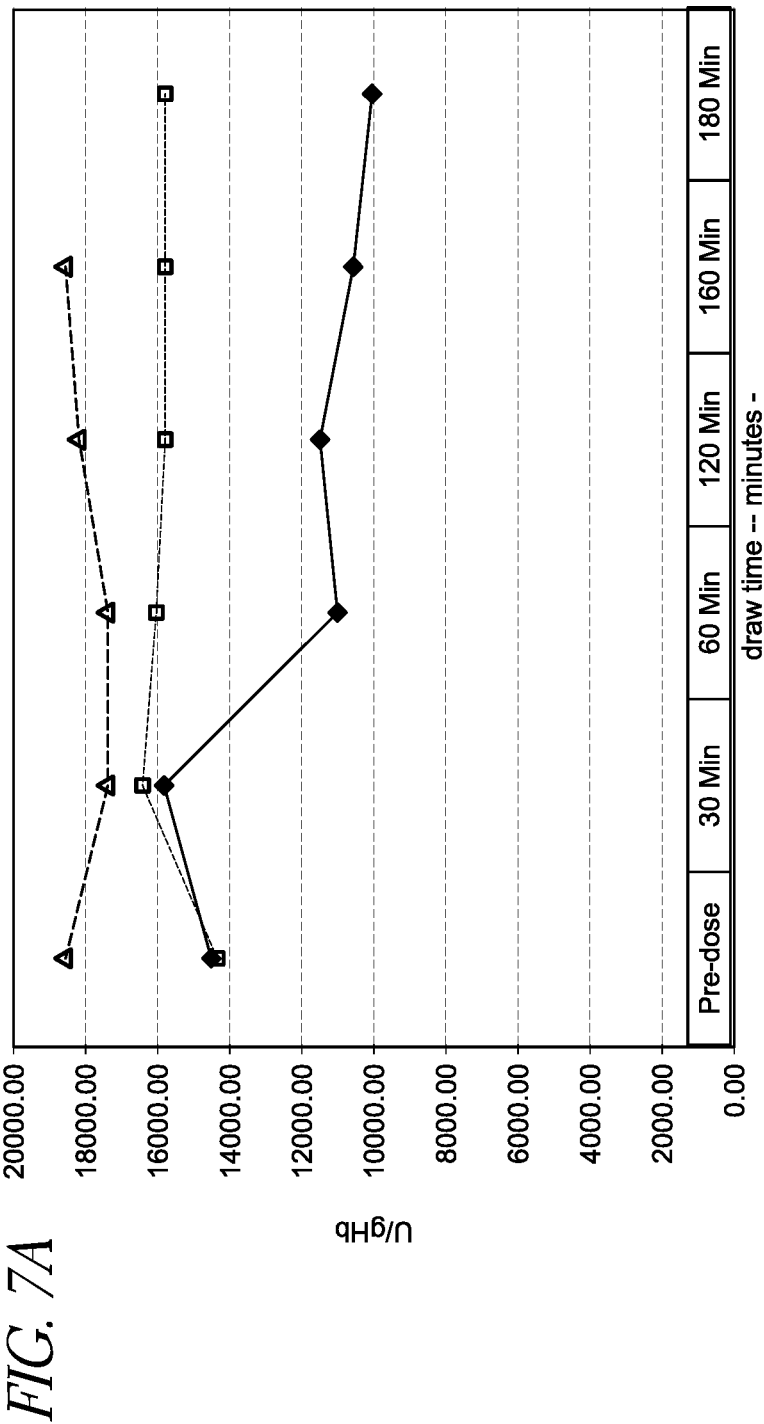
FIG. 7A-7B.
Figure 7B:
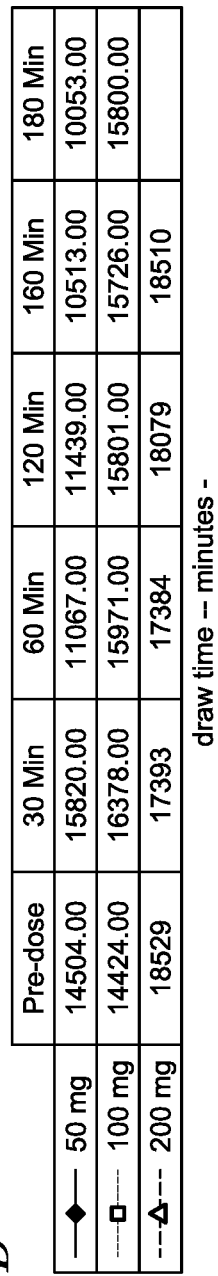

Researcher self-administered topical Glutathione after receiving a low blood Glutathione reading (FIG. 6A/B). Researcher observed an almost immediate improvement in symptoms of fatigue and drowsiness. After 70+ days a repeated intracellular Glutathione reading showed an increase to normal (FIG. 7A/B). Clinically, researcher had lost about 10 pounds, and experienced a noticeable increase in energy, along with a significant increase in mental clarity.

Gel form topical Glutathione was then administered to patients enrolled in various mini-clinical trials. Clinically results included resolution of light skin wrinkles at the application site, increase in energy levels and focus, dramatic increase in mental clarity, a 2.5 point (on average) drop in HbA1C with diabetic patients (in first 30 days—approximately 10 patients were tested and showed a significant change in HbA1C), a decrease in abnormal liver function tests in patients with a large variety of liver problems, increase in stamina and exercise tolerance/endurance, an average 5 lb. weight loss in first 30 days, self-reported clinical improvement of muscle and joint pain when applied to specific joints including hands, feet, and knees. The mini-clinical trial results were consistently observed by both the patients themselves and the researcher.

TABLE 1

| | Results | | |
|---|---|---|---|
| Micronutrients | Patient Results (% Control) Before | Patent Results (% Control) After | Reference Range (greater than) |
| Antioxidants | | | |
| Glutathione | 38 (Deficient) | 50 | >42% |
| Cysteine | 49 | 47 | >41% |
| Coenzyme Q-10 | 92 | 86 (Deficient) | >86% |
| Selenium | 84 | 79 | >74% |
| Vitamin E (A-tocopherol | 90 | 90 | >84% |
| Alpha Lipoic Acid | 90 | 89 | >81% |
| Vitamin C | 62 | 63 | >40% |
| SPECTROX ™ | | | |
| Total Antioxidant Function | | 73 | >65% |

Example 5: Reduced Glutathione (RealGSH™) Studied Benefits

Dosing Study—Though RealGSH™ can be made at concentrations per milliliter of 50 to 950 milligrams there seemed to be little difference in the higher doses versus 100 mg/ml. Dosing studies were performed using the same person (prevented confounding via skin variations) and applying several different doses. It was important to note that this study continued to 4 hours but the levels did not level off at the end of the 4 hours—and may have continued to elevate.

Intracellular Levels Increase—with topical application for approximately 5 weeks one 50 year old patient whose intracellular levels were low (tested through Spectracell™ out of Texas) showing signs of fatigue and mental fog, had a complete resolution of symptoms and then at 5 weeks showed a significant rise in intracellular GSH levels with follow-up repeat Spectracell™.

Burn Pain Reduction—Due to the molecular binding capability of the GSH molecule researcher's noted a significant (usually 100%) almost instantaneous decline in pain post burn (sunburn, household burn, or sunburn) when applied directly to the burn site. This is of course limited to First and Second Degree burns. The burn also appears to heel much more quickly with less scarring.

Muscle and Joint Pain Reduction—On over 300 patients it was noted that approximately 99% had a dramatic decrease in overall pain with daily use, most within the first few minutes. Most were able to indicated they wished to stop all pain meds including narcotics and appeared to do so without any ill withdrawal effects or otherwise.

Detoxification Capabilities—36 patient double-blinded study. Started with 24 hour urine collected for Quantitative Heavy Metals, which were all normal followed by a repeat 24 hour urine collected for Quantitative Heavy Metals, which showed in more than 91% of cases that there was a significant increase in heavy metal output in the urine when our RealGSH™ was applied (we did not use a controlled amount or dose). The 10 patient control showed no increase in their second urine but then they were crossed back over to the study group where they showed a significant increase.

Alcohol Detoxification Capabilities—In repeat studies volunteers could not become intoxicated when RealGSH™ was applied before imbibing. Volunteers who got intoxicated (not applying the RealGSH™) who then applied the RealGSH™ would then become sober in approximately 34½ minutes on average.

Improvement in Chronic Renal Failure—Two patients (one in her 70s and the other in his early 30s) with diagnosed CRF (Chronic Renal Failure with GFRs<30) both had improvement back to a normal GFR (>50) within a month of daily use of RealGSH™.

Improvement in Acne Pustule Formation, Reduction in Inflammation and Scarring—In a 5 patient study with Grade 1-3 facial acne there was dramatic decrease in pustule formation and inflammation plus noticeable fading of scars. This was documented with both questionnaires and close-up digital photography.

Arthritis Symptom Improvement—Consistently patients noticed clinical improvement in their joint inflammation and increased range of motion upon application. This occurred with both weight bearing joints (knees and ankles) and fine joints (such as in the hands). WE think this and many of these other observations are due to the sticky nature of the RealGSH™ reduced glutathione at a molecular level apparently binding inflammatory cytokines.

Increased Wellbeing—Vast majority of patients who used RealGSH™ reported a marked improvement in their sense of well-being.

Increased Mental Clarity—Vast majority of patients who used RealGSH™ reported a marked improvement in their mental clarity—this does not seem to be age related.

Depression Improvement—Vast majority of patients who used RealGSH™ reported a marked improvement in their depression symptoms.

Reflex Sympathetic Dystrophy (RSD) Pain Resolution—In one patient (case report pending) marked improvement in lower extremity Reflex Sympathetic Dystrophy (RSD) occurred with multiple daily applications of RealGSH™ to the site. This is significant because RSD is considered to be one of the most painful disorders one can have and is basically considered almost untreatable. This goes along with the other improvements in pain noted above in #4. The pain reduction (from a 9+ to a 1-2) began on the first day of therapy—was documented daily with questionnaires filled out by the patient (a 53 year old teacher on her feet all day).

Rapid Improvement in HbA1C in Type 2 Diabetics—HbA1C is a 3-6 month cellular "look back" on your average blood sugar levels. With application of RealGSH™ in approximately 10 Type 2 diabetics reported a significant (and somewhat unexplainable) drop in their HbA1C levels (from 0.7-2.0) would occur in the first 30-45 days. Despite RBC cell life questions (theoretically what we saw consistently should not have happened in such a short time) we considered this to be a very significant benefit of RealGSH™, maybe one of the most important.

Marked Lowering of Triglyceride Levels (beyond the capabilities of a statin)—In 7 patients with hypertriglyceridemia formerly treated with various statins, after discontinuation of the statins and daily application of the RealGSH™, an improvement of triglyceride levels (50 points lower on average) were noted in the 7 patients. No side effects were noted.

Improvement in LFTs in Hepatitis C patients in Liver Failure—In 2 patients in liver failure (awaiting transplant) with LFTs (Liver Function Tests) in the 10,000+ range, after 30 days of application of RealGSH™, their LFTs returned to normal. No viral counts were obtained pre or post application but studies continue.

Example 6: Second Degree Burn With Dramatic Healing After Application of Nanonized GSH; Case Report A second degree burn affects the epidermis and the dermis, classified as superficial or deep according to the depth of injury. The superficial type involves the epidermis and the papillary dermis and is characterized by pain, edema, and the formation of blisters; it heals without scarring. The deep type of burn extends into the reticular dermis, is pale and anesthetic, and results in scarring. Topical stable ranonized GSH is a pharmaceutical grade product (RealGSH™ produced in the USA by The Glute Group, LLC of Utah) that involves a Japanese (BioKyowa™) natural reduced glutathione (GSH) encased in a nano ($\gamma$-cyclodextrin ring from Cavamax™ in Germany) ring, the encasement of which involves a process patent (currently pending). This has been placed in a sterile hydrous solution for topical application (from which it may be easily applied). In testing this product caused no known side effect and its components (GSH and ring) are considered GRAS certified by the FDA.

A 50 year old woman accidentally received a second degree burn on her left clavicle after lifting a pan of boiling water off her stove too quickly. She rated her pain post burn as 10 (on a scale of 0-10) when questioned and so immediately applied a lavender essential oil to alleviate some of the pain but a few days later blisters had formed and the pain was still an 8 especially with movement. Coincidentally she presented to our office to take part in a detox trial being run on a new topical stable nanonized GSH (RealGSH™) to determine heavy metal movement in 24 hour urine samples with topical application. At our suggestion she decided to apply it topically to the burn (numerous articles on burns had shown how they could improve with GSH). The following are her diary notes of what happened afterwards:

"DAY 1: 04.13.12

Pain level 8 (caused during movement through scar being pulled during walking, etc. She reported that she had to keep her shoulder still to avoid pain.).

First and second application: applied to the burn site every couple of hours. By the second application the burn literally dried up and began to flake off. At one point I lifted off a brownish flake that was the size of a penny. I was shocked! Pain level had dropped to a 0-2 almost immediately upon application.

DAY 2: 04.14.12

Pain level 5 Caused during movement. Patient was able to begin moderate movement of the shoulder. The blisters that had only begun to harden the day before had become small scabs. After the first application of glutathione on the burn, one of the scabs fell off in researcher's fingers. Images show that by the second application, the second blister/scab began to lift off.

DAY 3: 04.15.12

Pain level 0" The clinical picture showed a partial to full thickness very tender and painful second degree blistering burn with some eschar formation when the patient first appeared. Clinical evaluation was performed daily thereafter with noticeable improvement but the most significant finding is patient's sudden decrease in pain with the application of the RealGSH™. Of note the patient has a history of fibromyalgia and adrenal insufficiency (all felt to be related to pituitary dysfunction) but is only on natural therapies—her surgical history is unremarkable. Patient's detox study results showed significant urinary arsenic output. Almost complete resolution (the bum turned to pink new skin on Day 3 as noted above and in photos) with no pain occurred by Day 3.

This case illustrates that the treatment not only helps reduce or even alleviate pain from these bums but accelerates healing and reduces scar formation. Both glutathione and the cyclodextrin ring have been ruled as GRAS/E certified (Generally Regarded As Safe Effective) by the FDA Glutathione has been theorized in numerous review articles (including NIH reviews) to perform a large number of healthy functions including increase photo-protection of sunburned cells but since there has not been a version that is actually stable and reduced and topical (now in consideration the only way, other than intravenously, that reduced glutathione can be added to the body—when taken orally the oxidized or reduced version is immediately digested becoming almost useless or some people do not have the ability to make GSH) until RealGSH was developed. The size of the nano particles of RealGSH™ are 7.5-8.15 Angstroms in diameter which are readily and easily absorbed through the skin matrix where the cyclodextrin rings (actually just a sugar) are broken down by enzymes, allowing the GSH to readily move intracellularly or into the blood stream for a rapid response as seen in this patient.

Researcher recommends further study and clinical evaluations as this could become an important therapy in the treatment of first and second degree burns and possible prevention of partial burn advancement to third degree especially in the area of post-bum pain relief.

Example 7: Reduction in HbAIC in Type 2 Diabetic with Topical Stable Nanonized Reduced Glutathione—A Case Report Type 2 Diabetes is a condition characterized or caused by a decline in functionality of the insulin receptors on the cell surface. GSH (reduced glutathione—the active form of glutathione) depletion has been shown to impair glucose tolerance. The reverse then should hold true—increasing the amount of GSH in the body should improve insulin receptor function. Topical stable nanonized GSH is a Patented pharmaceutical grade product (RealGSH™ produced in the USA by The Glute Group, LLC of Utah) that involves a Japanese (BioKyowa™) natural reduced glutathione (GSH) encased in a nano (γ-cyclodextrin ring from Cavamax™ in Germany) the encasement of which involves a process patent (currently pending). This is then placed in a sterile hydrous solution for topical application (from which it is easily applied). This product causes no known side effect and its components (GSH and ring) are considered GRAS certified by the FDA Researchers believe from their previous work and other research (NIH review articles, etc.), that reduced GSH has been determined to be significantly reduced in diabetics and has been postulated to lower glycosylated hemoglobin—but an easily utilizable effective stable GSH has not been previously available.

A 64 year old male patient with Type 2 Diabetes (ten plus years duration) who was on no medications and was poorly controlled via diet was given topical stable nanonized GSH at 200 mg/ml and advised to apply 2 squirts twice a day (approximately 1 ml a day or 200 mg) for fifty (i.e. 54) days and then retested. No other medications or changes occurred in his therapy during this time. His HbAIC dropped 0.7 point in 30 days, a noticeable improvement.

Decreases of 2 points or greater have also been seen but are strictly anecdotal at this point. If this were helpful in Type 2 Diabetes it would be a relatively inexpensive, side effect free, highly beneficial therapy that is easy to apply and helpful in many other ways (as an anti-oxidant, potential prevention against macular degeneration, etc.).

Example 8: Reflex Sympathetic Dystrophy Improved with Topical Stable Nanonized GSH—A Case Report Reflex Sympathetic Dystrophy is one of the most painful and debilitating condition known in medicine. Complex Regional Pain Syndrome (CRPS), also known as Reflex Sympathetic Dystrophy, is a chronic neurological syndrome characterized by severe burning pain, pathological changes in bone and ski, excessive sweating, tissue swelling, and extreme sensitivity to touch.

There are Two Types of CRPS—Type I and Type II. CRPS Type I (also referred to as RSD)—involve cases in which the nerve injury cannot be immediately identified. CRPS Type II (also referred to as Causalgia)—cases in which a distinct "major" nerve injury has occurred. CRPS is best described in terms of an injury to a nerve or soft tissue (e.g. broken bone) that does not follow the normal healing path. CRPS development does not appear to depend on the magnitude of the injury. The sympathetic nervous system seems to assume an abnormal function after an injury. Since there is no single laboratory test to diagnose CRPS, the physician must assess and document both subjective complaints (medical history) and, if present, objective findings (physical examination). It is usually considered only treatable with pain alleviation such as chromic narcotic use and other pain management therapies. Topical stable nanonized GSH is a patented pharmaceutical grade product (RealGSH™ produced in the USA by The Glute Group, LLC of Utah) that involves a Japanese (BioKyowa™) natural reduced glutathione (GSH) encased in a nano (γ-cyclodextrin ring from Cavamax™ in Germany) ring, the encasement of which involves a process patent (currently pending). This is then placed in a sterile hydrous solution for topical application (from which it is easily applied). This product causes no known side effect and its components (GSH and ring) are considered GRAS certified by the FDA Researchers believe from their own previous work and other research (NIH review articles, etc.) that reduced GSH had aggressive molecular binding capabilities—enabling it to bind and remove from the body (via the kidneys) just about anything that should not be there (including, we hoped, inflammatory cytokines and pain mediators). GSH has also been determined to be reduced in neuropathic pain so elevating levels would hopefully alleviate the pain and RealGSH™ has been shown upon application to immediately elevate skin and tissue levels of GSH.

This patient was a 54 year old school teacher who had been a Type 2 Diabetic for 20 years (oral controlled) and had received the diagnosis of RSD (CRPS Type I) ten years prior when she a underwent a second toe amputation on the right foot. Her blood sugars were well controlled but her pain was becoming intolerable and she had been considering a nerve block and "spinal procedure" when she presented. The compounded topical nanonized stable reduced GSH was prescribed with almost immediate improvement (a daily questionnaire log was kept by the patient. Pain dropped from a 9+most days to 1-2 and became very tolerable. She had to apply the GSH every four hours but had no problem with application. She reported being able to ambulate and stand on it (she taught math at a high school) and that it had changed her life. Her pain most days is now 0-1 and she reports is very tolerable. This treatment shows promise as new therapy to aid in the care of these patients.

Example 9: Response of Blood GSH Levels to Transdermal Stabilized Glutathione; Dosing Case Study The purpose of this cohort was to measure Glutathione levels only, as measurements were for single doses and not extended treatment. Studies followed the procedures of a complete and formal research protocol, available upon request from RealGSH™. One purpose was to determine whether or not reduced glutathione penetrated the skin in a useable form.

The test subject was a 51 y/o cau male who had no previous exposure to GSH or GSH enhancing compounds applied topically, orally or otherwise. The test subject's past medical history was as follows:

Primary hypertension, primary hypercholesterolemia, cholelithiasis, gastric ulcers, kidney stones, diagnosed as "pre-diabetic", tension headaches, migraine headaches, psoriasis, ankylosing spondylitis and intermittent arthritis. The subject had used Ibuprofen, and Extra strength Tylenol used PRN for occasional headaches and was not using vitamins or supplements. There was no report of past surgical history. Subject had no known allergies.

Baseline blood GSH levels were drawn as well as safety lab's consisting of CMP, urinalysis, CBC, lipid profile and HbA1C. 1 ml of the 50 mg/ml GSH gel was applied to an area of clean skin and a chronological series of blood samples were drawn to determine if plasma GSH levels rose, fell or remained unchanged. The levels were drawn pre-dose, 30 min, 60 min, 120 min, 160 min and 180 min. The subject was sent home for a 3 day "washout" period and the same protocol was performed on the 100 mg/ml gel and then after a 3 day "washout" the same protocol was performed on the 200 mg/ml gel.

Glutathione gel was applied to an area of approximately 60 square centimeters on the inside of the lower forearm. Prior to applying glutathione gel the site was washed with soap and water and dried with a towel to eliminate any contaminating residue on the skin.

The first dose was applied at: 10:33 AM (50 mg)
The second dose was applied at: 11:25 AM (100 mg)
The third dose was applied at: 11:07 AM (200 mg)

Since the mechanical spray during testing did not always administer 100% accurate dosing the administrator manually measured the dose into a small measurable plastic graduated cylinder. The amount of glutathione product liquid to equal 50 mg for the first dose was precisely measured. The measurement was verified by the measurable applicator, which was a pipette. The entire liquid drawn up in the pipette was applied to the forearm and rubbed in by the subject. This same process was used to measure out the 100 mg and the 200 mg dose. Blood levels/samples obtained via blood draw in the anticutibal space of the arm. The only change observed from the subject's baseline assessment was fatigue that lasted for approximately 7 hours the evening of the first dose. It spontaneously resolved on its own.

Results:

The application of a single dose, (1 ml topical stabilized GSH gel) of the 200 mg/ml compound saw an increase in blood GSH of +392 μmol/L over a period of 180 minutes. The application of a single dose, (1 ml topical stabilized GSH gel) of the 100 mg/ml compound saw an increase in blood GSH of +102 μmol/L over a period of 180 minutes. The application of a single dose, (1 ml topical stabilized GSH gel) of the 50 mg/ml compound saw a decrease in blood GSH of −70 μmol/L over a period of 180 minutes. This decrease could be caused by innumerable variables or by countless physiological processes and will not be discussed here. (FIG. 6A/B).

Figure 8A:
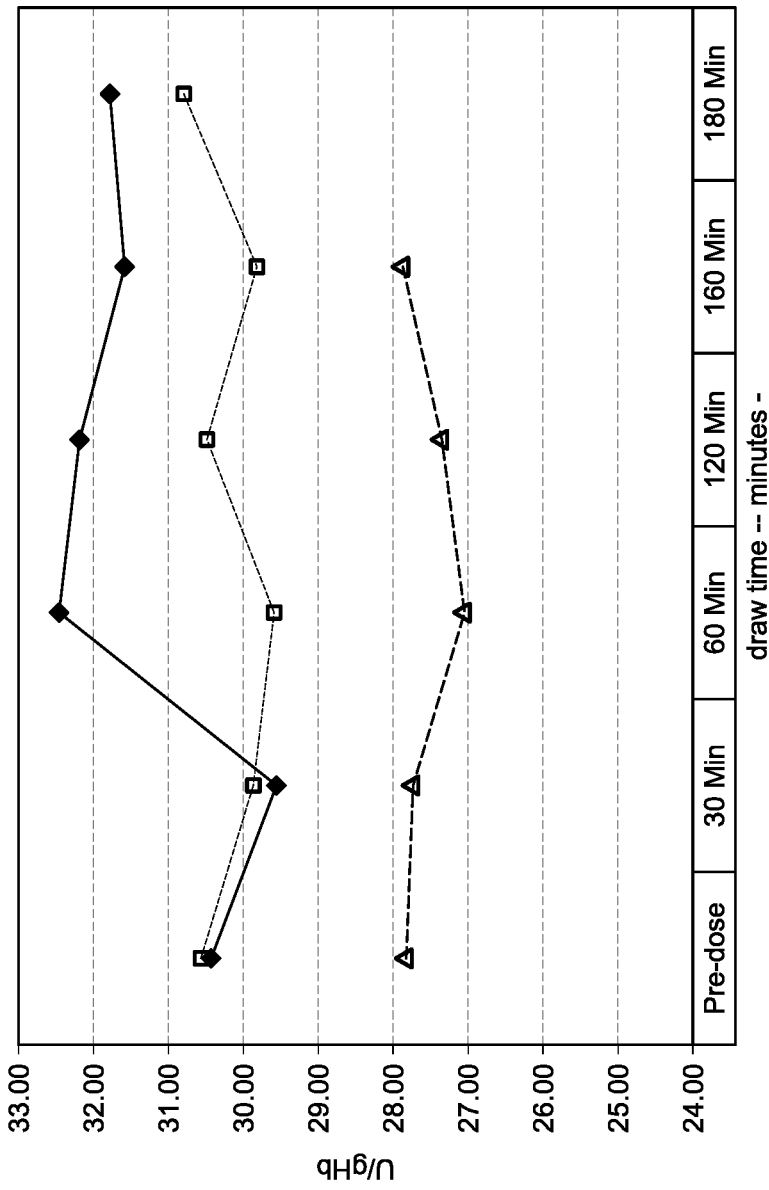
FIG. 8A-8B.
Figure 8B:
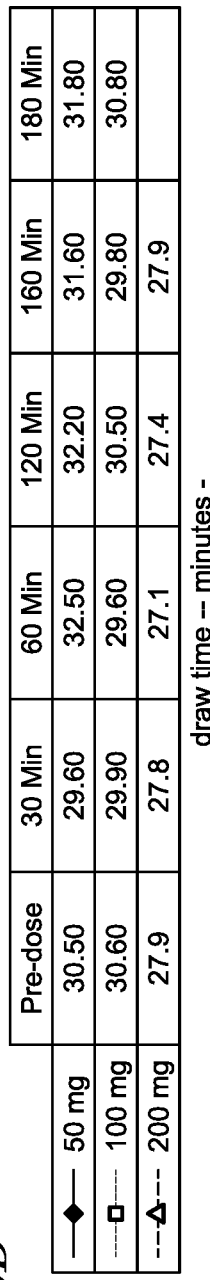
Figure 9A:
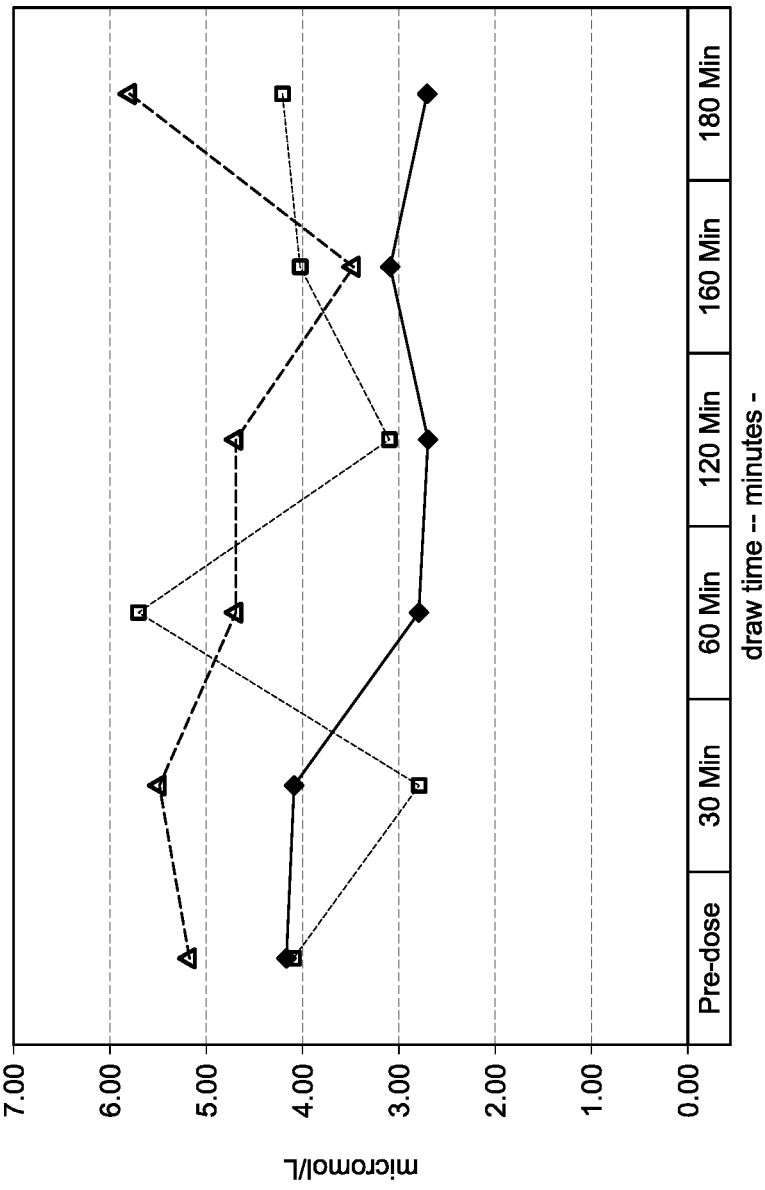
FIG. 9A-9B.
Figure 9B:
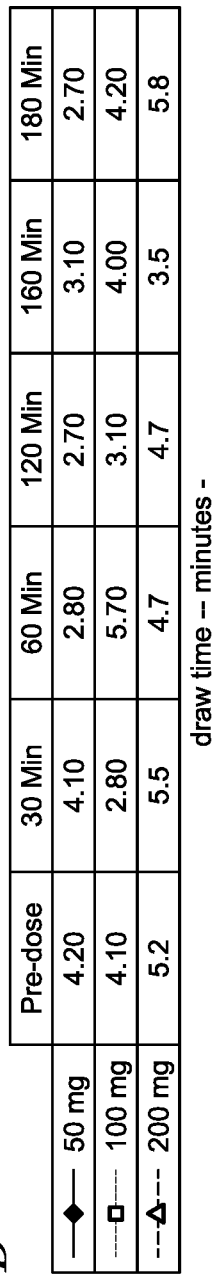

Blood level readings were also taken for superoxide dismutase (FIG. 7A/B), glutathione peroxidase (FIG. 8A/B), and lipid peroxidase (FIG. 9A/B) at 30, 60, 90, 120 and 180 minutes following doses of 50 mg/ml, 100 mg/ml, and 200 mg/ml.

The study indicated that usable reduced glutathione entered the blood transdermally, impacting blood glutathione levels as well as levels of related molecules. Therefore, this compound appears to cross the dermal barrier and may be pharmaceutically useful as well as useful in significantly lower doses including in cosmetics, antioxidant creams and numerous other nutraceutical formulations.

Example 10: 34 Volunteer Nanonized GSH Double Blinded Detox Study-Synopsis

It was proposed that nanonized topical stable highly reduced glutathione would act as a detoxification agent potentially removing heavy metals. It is unknown as to what percentage of the population suffers from heavy metal toxicity. There is no known natural heavy metal detoxificant so detoxification could potentially be of interest for patients of kidney or liver disease with broader implications regarding various neurological disorders. Topical stable nanonized GSH is a patented pharmaceutical grade product (RealGSH™ produced in the USA by The Glute Group, LLC of Utah) that involves a Japanese (BioKyowa™) natural reduced glutathione (GSH) encased in a nano (γ-cyclodextrin ring from Cavamax™ in Germany) ring, the encasement of which involves a process patent (currently pending). This was then placed in a sterile hydrous solution for topical application (from which it is easily applied). This product caused no known side effect and its components (GSH and ring) are considered GRAS certified by the FDA.

Figure 13:
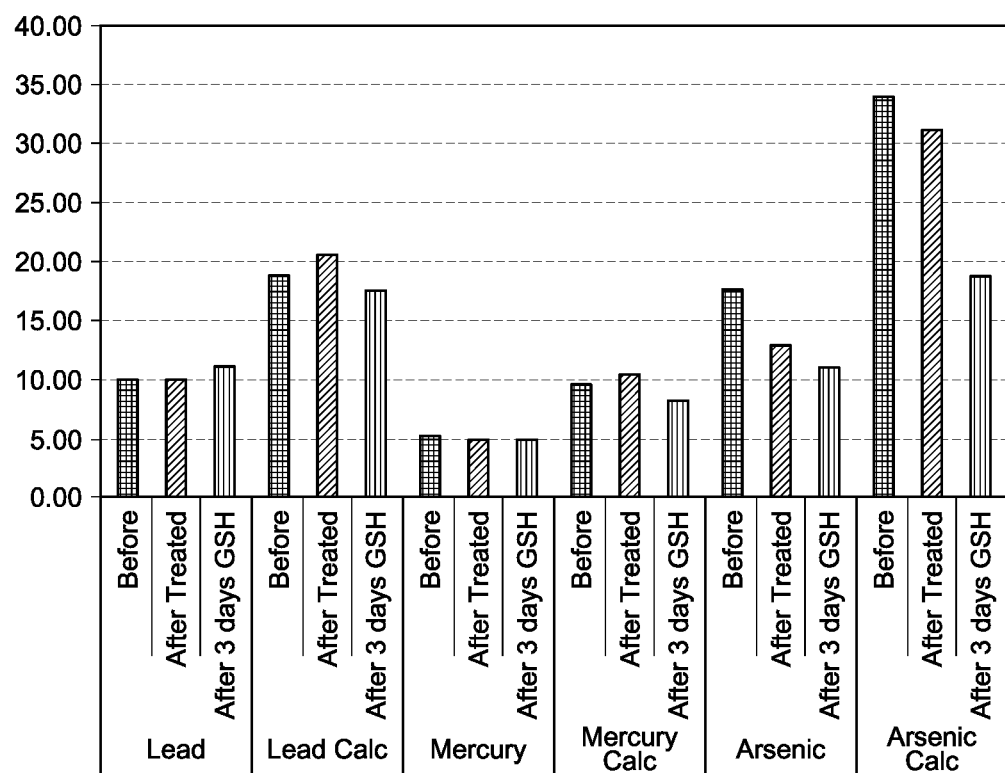
FIG. 13 is a bar graph depicting a numerical summary of urinary output and calculated urinary output of lead, mercury, and arsenic in a 10 volunteer placebo group before intervention, after receiving a placebo and after treatment with GSH, as measured by Electrothermal (Flameless) AAS and Mercury Hydride procedure through Mountain Star Clinical Laboratories. (Example 10).

The study involved 34 volunteers who were brought in in three groups. The volunteers collected urine for 24 hours in order to obtain a baseline urinalysis for quantitative heavy metals involving lead, mercury, and arsenic—testing used was an Electrothermal (Flameless) AAS and Mercury Hydride procedure through Mountain Star Clinical Laboratories was utilized in this study. On Day #2 the volunteers were given nanonized topical stable highly reduced glutathione (RealGSH™) at 100 mgm/ml and told to apply it liberally throughout the day. They were instructed to wash off between applications but to be liberal in their applications. The study was double blinded but then was un-blinded and the volunteers given placebo were crossed back over and followed for three days and then given the third 24 urinalysis on Day #3. (FIGS. 12 and 13).

Figure 11:
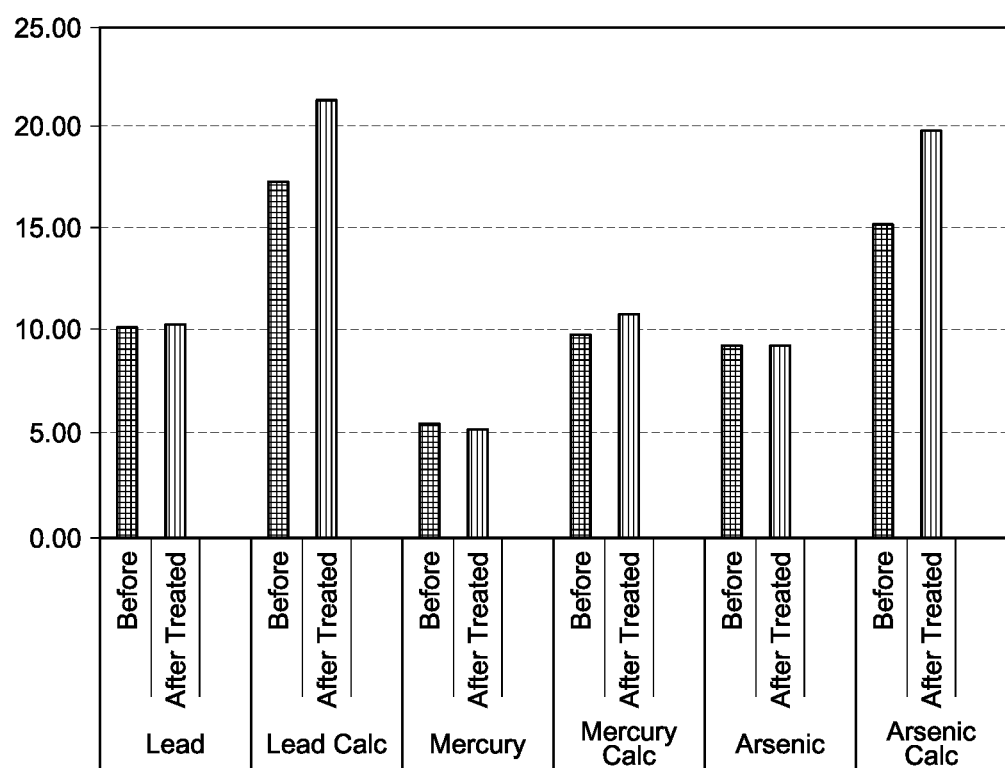
FIG. 11 is a bar graph depicting a numerical summary of urinary output and calculated urinary output of lead, mercury, and arsenic in 24 treated volunteers, within a 34 volunteer study, before and after treatment with GSH, as measured by Electrothermal (Flameless) AAS and Mercury Hydride procedure through Mountain Star Clinical Laboratories. (Example 10).

Results: Approximately 75% of patients showed an increase in heavy metal output on Day #2 (the day that the nanonized GSH was applied) (FIGS. 10 and 11). 60+% of the placebo crossovers showed a dramatic decrease in urine output of heavy metals (many from toxic levels during Day #1 and placebo Day #2) on Day #3 (when they applied the nanonized GSH) (FIGS. 12 and 13). This formulation of nanonized glutathione has also been shown to cause improvement in kidney function in a number of patients anecdotally.

Conclusions: This formulation of nanonized glutathione appears to be a fairly effective heavy metal detox agent.

TABLE 2

Results of Before and After Study

| Person | Lead Before | Lead After | Lead Calc Before | Lead Calc After | Mercury Before | Mercury After |
|---|---|---|---|---|---|---|
| 1 | 10 | 10 | 28 | 28 | 5 | 5 |
| 2 | 10 | 10 | 10 | 13 | 5 | 5 |
| 4 | 10 | 10 | 19 | 21 | 6 | 6 |
| 5 | 10 | 10 | 20 | 29 | 7 | 5 |
| 6 | 10 | 10 | 19 | 18 | 6 | 5 |
| 7 | 10 | 10 | 16 | 35 | 5 | 5 |
| 8 | 11 | 10 | 17 | 30 | 5 | 5 |
| 9 | 10 | 10 | 9 | 12 | 5 | 7 |
| 14 | 10 | 10 | 22 | 14 | 5 | 5 |
| 15 | 10 | 10 | 16 | 15 | 5 | 5 |
| 19 | 10 | 10 | 16 | 17 | 5 | 5 |
| 20 | 10 | 10 | 12 | 14 | 5 | 5 |
| 21 | 10 | 10 | 22 | 20 | 6 | 5 |
| 22 | 10 | 10 | 27 | 36 | 8 | 5 |
| 23 | 10 | 10 | 26 | 27 | 6 | 5 |
| 24 | 10 | 10 | 23 | 17 | 9 | 7 |
| 25 | 10 | 12 | 12 | 7 | 5 | 5 |
| 26 | 10 | 11 | 14 | 11 | 5 | 5 |
| 28 | 11 | 10 | 16 | 17 | 5 | 5 |
| 30 | 10 | 10 | 24 | 43 | 5 | 5 |
| 31 | 10 | 10 | 5 | 28 | 5 | 5 |
| 32 | 10 | 12 | 11 | 13 | 5 | 5 |
| 33 | 10 | 12 | 16 | 19 | 5 | 5 |
| 34 | 10 | 10 | 15 | 28 | 5 | 5 |
| Average of Treated: | 10.08 | 10.29 | 17.29 | 21.33 | 5.54 | 5.21 |

TABLE 3

Results of Before and After Study

| Person | Mercury Calc Before | Mercury Calc After | Arsenic Before | Arsenic After | Arsenic Calc Before | Arsenic Calc After |
|---|---|---|---|---|---|---|
| 1 | 14 | 14 | 17 | 20 | 47 | 56 |
| 2 | 5 | 6 | 17 | 21 | 17 | 26 |
| 4 | 12 | 12 | 5 | 8 | 10 | 15 |
| 5 | 14 | 15 | 5 | 5 | 10 | 16 |
| 6 | 11 | 9 | 12 | 5 | 23 | 9 |
| 7 | 8 | 17 | 10 | 7 | 16 | 24 |
| 8 | 8 | 15 | 5 | 5 | 8 | 15 |
| 9 | 5 | 8 | 24 | 14 | 22 | 16 |
| 14 | 11 | 7 | 5 | 5 | 11 | 7 |
| 15 | 8 | 7 | 7 | 5 | 11 | 7 |
| 19 | 8 | 9 | 6 | 5 | 9 | 9 |
| 20 | 6 | 7 | 5 | 5 | 6 | 7 |
| 21 | 13 | 10 | 7 | 5 | 16 | 10 |
| 22 | 22 | 18 | 7 | 7 | 19 | 25 |
| 23 | 16 | 14 | 8 | 8 | 21 | 22 |
| 24 | 20 | 12 | 5 | 27 | 11 | 45 |
| 25 | 6 | 3 | 15 | 12 | 18 | 7 |
| 26 | 7 | 5 | 9 | 5 | 12 | 5 |
| 28 | 7 | 8 | 13 | 12 | 9 | 24 |
| 30 | 12 | 22 | 14 | 15 | 33 | 65 |
| 31 | 3 | 14 | 5 | 7 | 3 | 19 |
| 32 | 5 | 5 | 5 | 5 | 5 | 5 |
| 33 | 8 | 8 | 5 | 5 | 8 | 8 |
| 34 | 8 | 14 | 12 | 11 | 18 | 31 |
| Average of Treated: | 9.88 | 10.79 | 9.29 | 9.33 | 15.13 | 19.71 |

TABLE 4

Results of Placebo Study

| Person | Lead Before | Lead Placebo | Lead After 3 days GSH | Lead Calc Before | Lead Calc Placebo | Lead Calc After 3 days GSH |
|---|---|---|---|---|---|---|
| 3 | 11 | 11 | 14 | 12 | 13 | 11 |
| 10 | 10 | 10 | 10 | 30 | 31 | 26 |
| 11 | 10 | 10 | 10 | 26 | 25 | 28 |
| 12 | 11 | 10 | 10 | 17 | 21 | 13 |
| 13 | 10 | 10 | 10 | 13 | 12 | 13 |
| 16 | 10 | 10 | 10 | 17 | 24 | 7 |
| 17 | 10 | 10 | 10 | 15 | 10 | 11 |
| 18 | 10 | 10 | 10 | 15 | 9 | 11 |
| 27 | 10 | 10 | 17 | 28 | 32 | 27 |
| 29 | 10 | 10 | 10 | 14 | 29 | 27 |
| Average: | 10.20 | 10.10 | 11.10 | 18.70 | 20.60 | 17.40 |

TABLE 5

Results of Placebo Study

| Person | Mercury Before | Mercury Placebo | Mercury After 3 days GSH | Mercury Calc Before | Mercury Calc Placebo | Mercury Calc After 3 days GSH |
|---|---|---|---|---|---|---|
| 3 | 5 | 5 | 5 | 5 | 6 | 4 |
| 10 | 5 | 5 | 5 | 15 | 16 | 13 |
| 11 | 5 | 5 | 5 | 13 | 13 | 14 |
| 12 | 5 | 5 | 5 | 8 | 11 | 6 |
| 13 | 5 | 5 | 5 | 7 | 6 | 6 |
| 16 | 6 | 5 | 5 | 10 | 12 | 4 |
| 17 | 6 | 5 | 5 | 9 | 5 | 5 |
| 18 | 5 | 5 | 5 | 8 | 4 | 3 |
| 27 | 5 | 5 | 5 | 14 | 16 | 14 |
| 29 | 5 | 5 | 5 | 7 | 14 | 13 |
| Average: | 5.20 | 5.00 | 5.0 | 9.60 | 10.30 | 8.20 |

TABLE 6

Results of Placebo Study

| Person | Arsenic Before | Arsenic Placebo | Arsenic After 3 days GSH | Arsenic Calc Before | Arsenic Calc Placebo | Arsenic Calc After 3 days GSH |
|---|---|---|---|---|---|---|
| 3 | 5 | 5 | 7 | 5 | 6 | 5 |
| 10 | 9 | 10 | 12 | 27 | 31 | 31 |
| 11 | 10 | 5 | 10 | 26 | 13 | 28 |
| 12 | 15 | 11 | 12 | 23 | 23 | 15 |
| 13 | 12 | 7 | 7 | 16 | 7 | 9 |
| 16 | 50 | 34 | 22 | 83 | 82 | 16 |
| 17 | 5 | 5 | 5 | 8 | 5 | 5 |
| 18 | 8 | 7 | 5 | 12 | 6 | 3 |
| 27 | 39 | 31 | 18 | 108 | 98 | 49 |
| 29 | 22 | 14 | 10 | 31 | 40 | 27 |
| Average: | 17.50 | 12.90 | 10.80 | 33.90 | 31.10 | 18.80 |

TABLE 7

Study Questionaire

| Question: | Number answering: | |
|---|---|---|
| | Yes | No |
| Change in Energy? | 7 | 5 |
| Change in well being? | 6 | 6 |
| Change in mental clarity? | 6 | 6 |
| Change in sleep? | 4 | 8 |
| Side effects? | 2 | 10 |
| Other benefits? | 5 | 7 |

Example 11: ESRD in a 30 Year Old Male Improved To Normal with Application of Topical Stable Nanonized Reduced Glutathione—A Case Report End-stage kidney disease (ESRD) is a chronic disease involving "the complete, or almost complete failure of the kidneys to function. The main function of the kidneys is to remove wastes and excess water from the body. This occurs when the kidneys are no longer able to function at a level needed for day-to-day life. It usually occurs when chronic kidney disease has worsened to the point at which kidney function is less than 10% of normal. ESRD almost always follows chronic kidney disease. A person may have gradual worsening of kidney function for 10-20 years or more before progressing to ESRD. Patients who have reached this stage need dialysis or a kidney transplant.

Topical stable nanonized GSH is a patented pharmaceutical grade product (RealGSH™ produced in the USA by The Glute Group, LLC of Utah) that involves a Japanese (BioKyowa™) natural reduced glutathione (GSH) encased in a nano (γ-cyclodextrin ring from Cavamax™ in Germany) ring, the encasement of which involves a process patent (currently pending). This is then placed in a sterile hydrous solution for topical application (from which it is easily applied). This product causes no known side effect and its components (GSH and ring) are considered GRAS certified by the FDA We believe from our previous work and other research produced (NIH review articles, etc.) reduced GSH is very aggressively sticky at a molecular level—attaching to and removing from the body (via the kidneys) just about anything that should not be there (including, we've found in other studies, heavy metals such as lead, mercury, and arsenic). GSH has also been determined to be reduced in CKD/ESRD so elevating levels would hopefully improve GFR. RealGSH™ has been shown upon application to immediately elevate skin and tissue levels of GSH.

This case involved a 30 year old male with idiopathic chronic pulmonary hypertension who had numerous radiographic tests requiring contrast media—the contrast media was felt to be most of the cause of his decline in renal function. He had a presenting GFR of 20 and creatinine of 2.85. The patient was told he would need to start on dialysis by a well qualified nephrologist at a local university hospital. Topical stable nanonized glutathione (aqueous or hydrous) gel was applied by the patient on a daily basis (approximately 200 mg a day) and the patient had serial GFRs and renal function testing performed. After approximately 4 weeks of application the creatinine returned to 2.19 and the GFR returned to a level of 34 (both WNL). This is improvement is presumably from the heavy metal removal secondary to increasing his serum glutathione levels but stoichiometrically seems to go beyond that. These results indicate that this treatment would be a simple and inexpensive way to improve renal function in patients with ESRD.

Example 12: Clinical Study of Nanoglutathione Gel 200 mg/cc; Dr. Michael H. Jensen, M.D The purpose of this report was to document pain relief with the use of topical Nanoglutathione. Over 200 patients were tested on Nanoglutathione gel 200 mg/cc during the past two years. Most of these were inpatients in long term care facilities, which allowed for continuing and accurate observation of results. This report explains the observed effects of the use of topical nanoglutathione gel on patients, particularly relative to pain. Nanoglutathione is pure glutathione that has been stabilized by a cyclodextrin ring and is used only topically. In concept, the glutathione is absorbed through the skin by the aid of the cyclodextrin ring and it has been demonstrated that actual glutathione levels rise significantly with this topical product. This report covers the most recent five month period and does not represent the entire patient base on which this product has been tested.

Pain scales used in are zero to ten, with zero being no pain and ten being maximal pain. Each pump "squirt" of Nanoglutathione represents 50 mg of Nanoglutathione.

"Shoulder" as used herein means the superior trapezius muscle unless otherwise indicated.

Patient #1: A 54-year-old male with symptoms of fibromyalgia documented by multiple doctors and this is a chronic problem. He was first treated with topical glutathione after an exacerbation of his fibromyalgia which is constant. The affected areas treated were neck, shoulders and rhomboids; when I refer to shoulders in each case I really mean the superior trapezius muscle. Pain scale before treatment was 8/10; pain scale after treatment was 5/10. This patient treated himself twice a day with three squirts of glutathione total. After three days his pain scale went to 3/10, and after two weeks 0/10. Duration of pain relief with first treatment was 4 hours, after two weeks 12 hours, and after three weeks 36 hours.

Patient #2: A 49-year-old male with myofascial pain of the neck and shoulders, and lumbar spine area status post fairly recent surgical fusion. The pain scale for neck and shoulders was 3/10, pain of the lower back 5/10. With two squirts of glutathione in each area this patient had no relief.

Patient #3: A 41-year-old female with well documented standard fibromyalgia. Pain scale was 6/10 and after treatment 0/10. Squirts of glutathione were to the trapezius and shoulders, two pumps per site; neck one pump. Length of relief was 4 to 6 hours. This patient treated several times a day. Results were not observed to be cumulative but patient experienced relief with each time treatment.

Patient #4: A 52-year-old male with acute trapezius and lumbar pain. Pain scale was 3/10, after treatment 0/10. Three squirts of glutathione were used. Time to relief was 5 minutes; length of relief was 8 hours.

Patient #5: A 23-year-old male who is a body builder with symptoms of myofascial pain of biceps and right olecranon tendinitis. Pain scale before treatment was 4/10 and after treatment 0/10. Squirts of glutathione were two to the biceps and two to the shoulders. Time to relief was 15 minutes. This patient received complete relief Symptoms returned following repeat of heavy body building routine, but each treatment gave complete relief of pain.

Patient #6: A 76-year-old female with longstanding pain of the right hip that is debilitating consistent with osteoarthritis. Pain scale before treatment was 5/10 and this pain was continuous. Pain scale after treatment was 0/10. Squirts of glutathione per treatment were two. Time until relief was 2 hours. Length of pain relief was 12 hours. This has been additive in that patient needs to repeat treatments only every several days.

Patient #7: A 52-year-old female with acute tennis elbow. Pain scale before treatment was 5/10. Pain scale after treatment was 2. Time to relief was 30 minutes. Length of pain relief was 3 hours.

Patient #8: A 52-year-old female status post ground level fall with whiplash type injury with pain of the neck and right shoulder. Pain scale before treatment was 7/10. Pain scale after treatment was 2/10. Squirts of glutathione were two total. Time to relief was 20 minutes. Length of pain relief was 5 hours. This patient used glutathione twice a day for two weeks and had complete relief of symptoms.

Patient #9: A 13-year-old female with lumbar pain with localized sciatica. Pain scale was 9/10, after treatment 4/10. Squirts of glutathione per treatment were four twice a day. Time to relief was 30 minutes. Length of relief was 5 hours.

Patient #10: A 43-year-old female with connective tissue disorder of the lumbar disks, or DJD, up her back and shoulder, fibromyofasciitis. Lumbar pain scale was 9/10 before treatment, after treatment 2/10. Shoulder and upper back pain 7/10, after treatment 2/10. Time to relief was 5 minutes. Length of pain relief was 4 hours.

Patient #11: A 43-year-old female with chronic lumbar pain with associated sciatica. She was status post L4-5 fusion. Pain scale before treatment 8/10 of the lumbar spine and 6/10 of the sciatica. After treatment lumbar pain was 0/10, the sciatica remained 6/10. Time to relief 10 minutes and squirts of glutathione were four.

Patient #12: A 54-year-old male with a right below-the-knee amputation with associated phantom pain for many years. Pain scale before treatment was 8/10, after treatment was 2/10. Squirts of glutathione per treatment were two, twice a day. Time to relief was 30 minutes. Length of pain relief was 8 hours.

Patient #13: A 77-year-old female with chronic lumbar pain. This patient notes degenerative joint disease of the lumbar spine, bone-on-bone, with left sciatic nerve pain. Lower back pain before treatment was 9/10, left hip or sciatic pain 9/10. After treatment, lumbar spine 3/10 and sciatic pain 3/10. Time to relief 6 minutes. Length of pain relief 4 hours.

Patient #14: A 43-year-old female with chronic left shoulder (left superior trapezius) pain. SI pain times 10 years. Pain scale of both these areas before treatment was 8/10, after treatment was 1/10. Time to relief 6 minutes. Squirts of glutathione were four total. Length of relief was 5 hours. This patient applied this twice a day and after two weeks she only applies glutathione to these areas once every five days. Her pain is 0/10.

Patient #15: A 56-year-old female with neck and shoulder myofasciitis, left knee pain and this patient also has wrinkles on her face for which she applies glutathione. Pain scale of the neck before treatment was 6/10, knee 7/10. After treatment neck pain was 2/10, knee pain 2/10. Squirts of glutathione to each area were two to face, two to neck and two to knee. Relief of pain of the neck and knee occurred in 15 minutes. She noticed increased muscle tone and decrease of wrinkles on her face in two weeks which is continuing. Length of pain relief was 6 to 8 hours in the neck and knee. After three weeks of twice a day treatment she used glutathione once every other day.

Patient #16: An 83-year-old male seen as an inpatient for right temporal postherpetic neuralgia. This patient appeared to be dying with a pain scale of 10/10 and was unable to eat. Pain before application to the right temporal area was 10/10, after 15 minutes was 2/10; this was the first application. Physician personally applied glutathione to this patient every Monday, Wednesday, and Friday. Patient had cumulative relief of pain over a period of three weeks and after a three week period of single applications to this area on Monday, Wednesday, and Friday needed treatment only once a week. Initially the patient's pain was so severe that even flicking the patient's hair triggered screaming. Physician had this patient also evaluated by neurosurgery who told Physician that there was nothing wrong with the patient following completion of the treatment regime. This patient continues to use glutathione once a week.

Patient #17: An 18-year-old, Polynesian, college football player with sprained left ribs after bench pressing and reps 450 pounds. Pain scale before treatment was 8/10, pain scale after treatment was 0/10. Squirts of glutathione were one squirt one time. Time to relief was 5 minutes. This patient had complete resolution of his pain. Of note, this injury did not occur over a single weight lifting session but he had had it for about two weeks and was still continued to bench press.

Patient #18: A 42-year-old female with bilateral SI pain and right hip pain for 10 years. Pain scale before treatment was 7/10, after treatment was 1-2/10. Squirts of glutathione were four total. These were applied by Physician. Time to relief was 10 minutes. Length of relief 60 hours. After two weeks of b.i.d. treatment she now only uses glutathione every five days.

Patient #19: A 64-year-old male with myofasciitis of the rhomboids lasting several weeks. Pain scale before treatment was 6/10, after treatment 2/10. Squirts of glutathione per treatment were six. Time until relief was 25 minutes. Length of relief was 6 hours. Physician personally applied glutathione once every Tuesday and Thursday. The results were additive though pain relief remained at a 2/10.

Patient #20: A 60-year-old female with severe chronic plantar fasciitis with associated neuropathy; osteoarthritis of the hands with associated neuropathy, and osteoarthritis of the knees. Pain scale with the plantar fasciitis before treatment was 8/10, after treatment 0/10. Pain scale of osteoarthritis of the hands with neuropathy before treatment was 6/10, after treatment 0/10. Pain scale of osteoarthritis of the knees before treatment was 6/10, after treatment 2/10. Time to relief in each case was 30 minutes. Squirts of glutathione were two per foot, one per hand and one per knee. Length of relief at the start was 24 hours, after two weeks she used gluitathione only three days. Of note, the neuropathy of her hands and of her feet was almost completely resolved to the point that stated it was barely detectable. This patient continues to use glutathione.

Patient #21: A 31-year-old female with right knee pain consistent with osteoarthritis. This patient weighed 300 pounds. She had knee pain roughly three times a year which lasted at least a month. Pain scale before treatment was 5/10, after treatment was 0/10. Time to pain relief was 30 minutes. Squirts of glutathione were four. Of interest, this patient only required one treatment and had no return of the pain. Physician continues to work with this patient three days a week.

Patient #22: A 72-year-old female with rheumatoid arthritis of the hands and major joints. Pain scale before treatment was generally 4/10 and then down to 1/10. Squirts of glutathione per treatment were five. Time until relief was 30 minutes. Length of pain relief was 8 to 12 hours. This has had an additive effect and the patient was able to decrease use of glutathione with the improvement in her hands.

Patient #23: An 82-year-old male with rheumatoid arthritis of the hands and major joints. Pain scale before treatment was 6/10, after treatment 1/10. Time until relief was 30 minutes. Squirts of glutathione per treatment were four. Length of pain relief was 12 hours. This patient now uses glutathione only once every several days.

Conclusions

Nanoglutathione treats many types of pain including myofascial pain. In Physician's experience with tension headaches, relief was in the 90th percentile. Fibromyalgia duration of relief was 2 to 4 hours with no cures but with remarkable improvement. Neurogenic pain, including two cases with one postherpetic neuralgia case. This was a very extreme case with the first application giving 90% resolution of pain. This patient had complete resolution of pain and continues to use glutathione once week. With plantar fasciitis Physician's experience has been 100% effectiveness. Osteoarthritis was difficult as these are deep tissues with varying results. Rheumatoid arthritis, there appeared to be a generalized improvement of 30-50%. Deep back pain consistent with degenerative disk disease, appeared to have 30-50% resolution requiring continued application.

Additionally, Physician experienced with two cases of second degree burns. Pain relief occurred within 5 minutes and healing time appeared to be cut in half.

Physician remarked that a significant percentage of his clinical population had dementia and he observed that in 10-15% of cases application of glutathione, four to six squirts, created a remarkable increase in mental acuity and wakefulness in all of these patients. Short term memory was also improved.

Example 13: RealGSH and Autism

It is known that approximately 50% of children born with autism spectrum disorder are unable to methylate. Thus they cannot produce glutathione. By age 2 1 h to 3 years they start to show signs of their autism which is actually secondary to heavy metal build-up internally in neurological tissue, which causes them symptoms of autism. Intravenous reduced glutathione (the only form previously thought to work) is too difficult and invasive to allow proper therapy with kids with autism. In one client intervention an 18 year old male, with advanced autism, had been placed in an Intermediate Care Facility for the Mentally Retarded (ICFMR) due to his paucity of speech (one word answers at most), inability to interact with others, and self-stimulation behavior. This client, after family approval, was given a trial of one dose a day of topical stable complexed glutathione (RealGSH) at approximately 200 mg a day. The study had intermediate videotaping of the patient (again with family release and approval) to document any potential improvement. Each week the participant met various improvement milestones and after 3 months of therapy (90 days) the participant was asking questions regarding where his family was, going shopping and making purchases and change, interacting normally with other members of the staff and other clients at the facility and elsewhere, and generally acting normally.

Example 14: RealGSH and Tardive Dyskinesia/Akathesia

Tardive dyskinesia is a difficult-to-treat form of dyskinesia, a disorder resulting in involuntary, repetitive body movements. In this form of dyskinesia, the involuntary movements are tardive, meaning they have a slow or belated onset. This neurological disorder frequently appears after long-term or high-dose use of antipsychotic drugs, or in children and infants as a side effect from usage of drugs for gastrointestinal disorders.

Tardive dyskinesia is characterized by repetitive, involuntary, purposeless movements. Some examples of these types of involuntary movements include grimacing, tongue protrusion, lip smacking, puckering and pursing of the lips, and rapid eye blinking. Rapid, involuntary movements of the limbs, torso, and fingers may also occur. In some cases, an individual's legs can be so affected that walking becomes difficult or impossible. Respiratory irregularity, such as grunting and difficulty breathing, is another symptom associated with tardive dyskinesia, although studies have shown that the prevalence rate is relatively low.

In one client intervention a 61 year old female, with severe tardive dyskinesia, had been placed in an long term care facility (nursing home) due to her severe tongue thrusting, inability to communicate, inability to ambulate, and mental confusion. This client, after family approval, was given a trial of one dose a day of topical stable complexed glutathione (RealGSH) at approximately 200 mg a day. The study had intermediate videotaping of the patient (again with family release and approval) to document any potential improvement. Each week the participant met various improvement milestones and after 3 months of therapy (90 days) the participant was speaking and asking questions regarding where her family was, normal standing and ambulation, going shopping and making purchases and change, interacting normally with other members of the staff and other clients at the facility and elsewhere, and generally acting normally. There is no effective therapy for tardive dyskinesia.

Example 15: Stabilization of Nano Glutathione

Stabilized Glutathione, antioxidant and Gamma Cyclodextrine complex was adjusted to a pH of not less than pH 4.00 and not more than pH 7.8, or not less than pH 5.00 and not more than pH 7.20 using Sodium hydroxide or hydrochloric acid. The solution was nanosized using Ultrasonic waves with appropriate ultrasonic equipment at about 100 Watts for not less than 1 minute and not more than 10 minutes, or less than 3 minutes and not more than 6 minutes. The resulting nanoparticles were not less than 20 angstroms and not more than 200 nanometers in size.

What is claimed is:

1. A method of treating an oxidative stress condition, comprising:
   topically applying to a subject affected by a condition associated with oxidative stress, an effective amount of a topical nanonized composition;
   wherein the composition comprises an inclusion complex comprising: reduced glutathione, an additional antioxidant, and gamma cyclodextrin;
   wherein the reduced glutathione is non-esterified, non-acetylated, and non-fatty acid attached;
   wherein the reduced glutathione is stabilized in a reaction mixture by bringing the reduced glutathione and the additional antioxidant in contact with the gamma cyclodextrin solubilized in a polar solution, wherein the molar ratio of reduced glutathione to gamma cyclodextrin is between about 4:1 and 13:1;
   wherein the additional antioxidant comprises at least one of the following: alpha-lipoic acid, ascorbic acid, uric acid, beta-carotene, alpha-tocopherol, dimethylethanolamine, CoEnzyme Q10, vitamin E, carnosine, catalase, superoxide dismutase, and peroxidase; and wherein ultrasonic waves nanonize the inclusion complex into nanoparticles;

wherein the nanoparticles have a particle size range between about 2 and about 200 nanometers; and wherein the topical application of the nanonized complex facilitates rapid absorption of the reduced glutathione into the bloodstream of the subject.

2. The method of claim 1, wherein the reaction mixture is capped under vacuum after mixing at a pH range of 3.0 to 7.0.

3. The method of claim 1, wherein the molar ratio of reduced glutathione to gamma cyclodextrin is between about 8:1 and 10:1.

4. The method of claim 1, wherein about 20% of the composition consists of reduced glutathione and about 10% of the composition consists of gamma cyclodextrin.

5. The method of claim 1, wherein the additional antioxidant is ascorbic acid at a concentration of about 4% by mass.

6. The method of claim 1, wherein the additional antioxidant is ascorbic acid and the weight ratio of reduced glutathione to ascorbic acid is about 5:1.

7. The method of claim 1, wherein the polar solution comprises ascorbic acid.

8. The method of claim 7, wherein the polar solution further comprises benzalkonium chloride.

9. The method of claim 1, wherein the composition is formulated as a liquid, cream, lotion, oil, emulsion, spray, aerosol, dissolving strip, bolus, or suppository.

10. The method of claim 1, wherein the composition is formulated as a liquid.

11. The method of claim 1, wherein the topical application comprises sublingual, transdermal, cutaneous, subcutaneous, mucosal, transmucosal, inhalation, intralesional, or buccal routes.

12. The method of claim 1, wherein the topical application comprises a transdermal route.

13. The method of claim 1, wherein the composition is administered to the subject twice daily.

14. The method of claim 1, wherein a daily dosage of the reduced glutathione is about 0.001 to 100 mg per kg of body weight of the subject.

15. The method of claim 1, wherein the condition associated with oxidative stress comprises type 2 diabetes.

* * * * *